United States Patent
James et al.

(10) Patent No.: US 12,102,723 B2
(45) Date of Patent: Oct. 1, 2024

(54) STERILIZING SYSTEM

(71) Applicant: VIRALCLEAN TECHNOLOGIES LLC, Commerce Township, MI (US)

(72) Inventors: Paul William James, Commerce Township, MI (US); Ken Ralston, Westland, MI (US); Deborah A. Kanter, Commerce Township, MI (US); William McClelland, Waterford, MI (US)

(73) Assignee: Viralclean Technologies, LLC, Commerce Township, MI (US)

( * ) Notice: Subject to any disclaimer, the term of this patent is extended or adjusted under 35 U.S.C. 154(b) by 472 days.

(21) Appl. No.: 17/554,331

(22) Filed: Dec. 17, 2021

(65) Prior Publication Data

US 2022/0193280 A1  Jun. 23, 2022

Related U.S. Application Data

(60) Provisional application No. 63/145,173, filed on Feb. 3, 2021, provisional application No. 63/126,689, filed on Dec. 17, 2020.

(51) Int. Cl.
*A61L 2/10* (2006.01)
*A61L 9/20* (2006.01)

(52) U.S. Cl.
CPC .................. *A61L 2/10* (2013.01); *A61L 9/20* (2013.01); *A61L 2202/11* (2013.01);
(Continued)

(58) Field of Classification Search
CPC .......... A61L 2/10; A61L 9/20; A61L 2202/11; A61L 2202/14; A61L 2202/16;
(Continued)

(56) References Cited

U.S. PATENT DOCUMENTS 6,656,424 B1  12/2003  Deal
8,481,985 B2   7/2013  Neister
(Continued)

FOREIGN PATENT DOCUMENTS

WO        90/05909       5/1990
WO    2015/026407 A1    2/2015
(Continued)

OTHER PUBLICATIONS

Far-UV Sterilray, Revolutionizing the World of UV: Far-UV Sterilray, https://sterilray.com, accessed Oct. 10, 2022.
(Continued)

*Primary Examiner* — Kiet T Nguyen
(74) *Attorney, Agent, or Firm* — The Dobrusin Law Firm, PC

(57) ABSTRACT

A light sterilizer comprising: (a) an ultraviolet-C (UVC) light secured to a light printed circuit board assembly (PCBA), wherein the UVC light projects a sterilizing zone to sterilize objects or surfaces within the sterilizing zone; (b) a heat sink positioned adjacent to and in contact with the UVC light, wherein the heat sink is mounted to the light PCBA; and (c) a fan positioned adjacent to the heat sink; wherein the UVC light sterilizes viruses within the sterilizing zone by breaking the virus molecules.

19 Claims, 10 Drawing Sheets

(52) U.S. Cl.
CPC ....... *A61L 2202/14* (2013.01); *A61L 2202/16* (2013.01); *A61L 2209/111* (2013.01); *A61L 2209/12* (2013.01)

(58) Field of Classification Search
CPC ........... A61L 2202/25; A61L 2209/111; A61L 2209/12; A61L 2209/16
USPC .................................................. 250/455.11
See application file for complete search history.

(56) References Cited

U.S. PATENT DOCUMENTS

| | | |
|---|---|---|
| 8,753,575 B2 | 6/2014 | Neister |
| 8,975,604 B2 | 3/2015 | Neister |
| 8,993,988 B2 | 3/2015 | Nathan et al. |
| 9,370,600 B1 | 6/2016 | DuPuis et al. |
| 9,597,420 B2 | 3/2017 | Maxik et al. |
| 9,687,575 B2 | 6/2017 | Farren |
| 9,700,642 B2 | 7/2017 | Neister |
| 11,116,857 B1* | 9/2021 | Benin ........................ A61L 2/24 |
| 11,246,951 B2 | 2/2022 | Neister |
| 2008/0253941 A1 | 10/2008 | Wichers et al. |
| 2009/0191100 A1 | 7/2009 | Deal |
| 2009/0272029 A1* | 11/2009 | Aiking ................... A23B 7/015  47/1.3 |
| 2010/0028201 A1 | 2/2010 | Neister |
| 2011/0272595 A1 | 11/2011 | Neister |
| 2014/0140888 A1 | 5/2014 | Neister |
| 2014/0227132 A1 | 8/2014 | Neister |
| 2016/0089459 A1 | 3/2016 | Boodaghians et al. |
| 2017/0304472 A1 | 10/2017 | Neister et al. |
| 2018/0343847 A1* | 12/2018 | Ervin ........................ A61L 2/10 |
| 2018/0353629 A9 | 12/2018 | Neister et al. |
| 2019/0201570 A1* | 7/2019 | Dobrinsky ........... G01N 21/645 |
| 2020/0030469 A1 | 1/2020 | Neister et al. |
| 2022/0133920 A1 | 5/2022 | Neister |
| 2022/0143232 A1 | 5/2022 | Neister |

FOREIGN PATENT DOCUMENTS

| | | |
|---|---|---|
| WO | 2016/049143 A2 | 3/2016 |
| WO | 2017/020028 A1 | 2/2017 |

OTHER PUBLICATIONS

Far-UV Sterilray™ Air Surface Disinfection Rail—YouTube; Mar. 8, 2019.

* cited by examiner

STERILIZING SYSTEM

CROSS-REFERENCE TO RELATED APPLICATIONS

This application claims the benefit of priority to U.S. Provisional Patent Application Nos. 63/126,689 filed on Dec. 17, 2020, and 63/145,173 filed on Feb. 3, 2021, the contents of which are incorporated herein by reference in their entirety.

FIELD

The present teachings generally relate to sterilizing system, and more particularly, to a sterilizing ultraviolet light trolley system.

BACKGROUND

There is an ongoing need for the sanitation and disinfection of surfaces and areas from bacteria, germs, spores, mold, fungi, pathogens, viruses, pollen, fumes, volatile organic compounds (VOCs), or a combination thereof. Due to current increased risks of viral infection, there is an even further demand for properly sterilizing surfaces and areas. To properly sterilize an area from viruses and other contaminants, the sterilization process must ensure damaging of the virus (e.g., damaging a nucleus of a virus), thereby eliminating the risk of infection for anyone present in the area or in contact with a previously contaminated surface. A similar process for sterilization must also be utilized for any other bacteria, germs, spores, mold, fungi, pathogens, viruses, pollen, fumes, VOCs, or a combination thereof.

Conventional sanitizing and/or disinfecting typically requires chemicals and/or germicides. These chemicals and/or germicides may be applied directly to a contaminated surface or used in aerosol form to spray a contaminated area. Unfortunately, such chemicals and germicides tend to lose their efficacy and may often not guarantee actual sterilization as discussed above, thereby leaving a risk of illness even after sanitizing and/or disinfecting. Additionally, such use of chemicals and/or germicides may ultimately lead to "superbugs" that are no longer responsive to such chemicals or germicides.

As an alternative to chemicals and germicides, ultraviolet (UV) light may be highly effective at killing contaminants on both surfaces and in the air. Unfortunately, conventional UV devices are often limited in either their efficacy, length of transmission, emission spectrum, or a combination thereof. Current UV devices may further require, during operation, frequent re-location as well as one or more optical filters, protective casings, guides for focusing and/or transporting the UV energy, or a combination thereof. As a result, such devices may only be utilized for limited areas or specific person effects, thereby making it highly difficult or even impossible to try and sterilize a larger area or room.

Thus, there remains a need for an alternative sterilizing device that effectively and efficiently sterilizes an area from contaminants. What is needed is a light sterilizer having a UV-C light that may break down contagious molecules, thereby eliminating the risk of infection. There also remains a need for a sterilizing device that can sterilize a much greater area of space in an efficient manner. What is needed is a light sterilizer or sterilizing system that can sterilize a larger area, such as an entire room.

SUMMARY

The present teachings meet one or more of the present needs by providing a light sterilizer comprising: (a) an ultraviolet-C (UVC) light secured to a light printed circuit board assembly (PCBA), wherein the UVC light projects a sterilizing zone to sterilize objects or surfaces within the sterilizing zone; (b) a heat sink positioned adjacent to and in contact with the UVC light, wherein the heat sink is mounted to the light PCBA; and (c) a fan positioned adjacent to the heat sink; wherein the UVC light sterilizes viruses within the sterilizing zone by breaking the virus molecules.

The light sterilizer may further include a reflector, wherein the UVC light is positioned within the reflector. The light PCBA may be positioned within a housing that at least partially encompasses the light PCBA and the UVC light. The light sterilizer may also include an LED light secured to the light PCBA, wherein the LED light indicates a status of the light PCBA. The LED light may be positioned within a reflector. Additionally, the reflectors may be secured to a housing of the light sterilizer.

The light sterilizer may also include a trolley that is configured to guide the light sterilizer along a track or cable system. The trolley may be located within the housing of the light sterilizer and the track or cable system may extend through a slot of the housing to engage the trolley. The light sterilizer may include a biasing member that biases the trolley against the track or cable system. The biasing member may be located within the housing of the light sterilizer. The light sterilizer may further comprise a driver located within the sterilizer housing that engages the track or the cable system, wherein the driver may be actuated by a drive motor to move the light sterilizer along the track or the cable system. The driver may engage a first side of a lip of a track and the trolleys may engage an opposing second side of the lip of the track.

Additionally, the heat sink and the fan of the light sterilizer may be contained within the housing of the light sterilizer, and the heat sink may be vented to an outside of the housing via a slot in the housing. Moreover, the reflectors may be tiltable, flexible, or both. It is also envisioned that the light sterilizer may include four or more UVC lights, and each of the UVC lights may create their own sterilizing zone. Each sterilizing zone may at least partially overlap with another sterilizing zone. The light sterilizer may also be controlled remotely via a mobile device, such as a mobile phone, tablet, computer, wireless remote, or a combination thereof. Moreover, the slot to vent the heat sink and the slot to receive the track or cable system may be positioned on different faces of the housing.

The present teachings may also meet one or more of the present needs by providing a sterilizing system comprising: (a) a light sterilizer according to any of the preceding claims; (b) an air sterilizer that circulates and sterilizes air within a desired area or room; (c) one or more room sensors, wherein the one or more room sensors detect the presence of a person within the desired area or room and communicates the detection with the light sterilizer. The air sterilizer may include: (a) an intake that receives the air from the desired area or room; (b) a sterilizing device within a housing of the air sterilizer that sterilizes the air received from the intake; and (c) a duct that distributes the sterilized air back into the desire area or room. The sterilizing device may of the air sterilizer may be a UVC light.

The one or more room sensors may each include a radar sensor and an infrared (IR) sensor. The light sterilizer may also include one or more position sensors to determine a position of the light sterilizer during movement along the track or the cable system. Additionally, the sterilizing system may include an emergency stop that allows a user to manually stop a cycle of the sterilizing system. Moreover, the light sterilizer, the air sterilizer, and the one or more room sensors may be in wired or wireless communication with one another.

Furthermore, the present teachings may meet one or more of the present needs by providing: an alternative sterilizing device that effectively and efficiently sterilizes an area from contaminants; a light sterilizer having a UV-C light that may break down contagious molecules, thereby eliminating the risk of infection; a sterilizing device that can sterilize a much greater area of space in an efficient manner; a light sterilizer or sterilizing system that can sterilize a larger area, such as an entire room; or a combination thereof.

DETAILED DESCRIPTION

Figure 1:
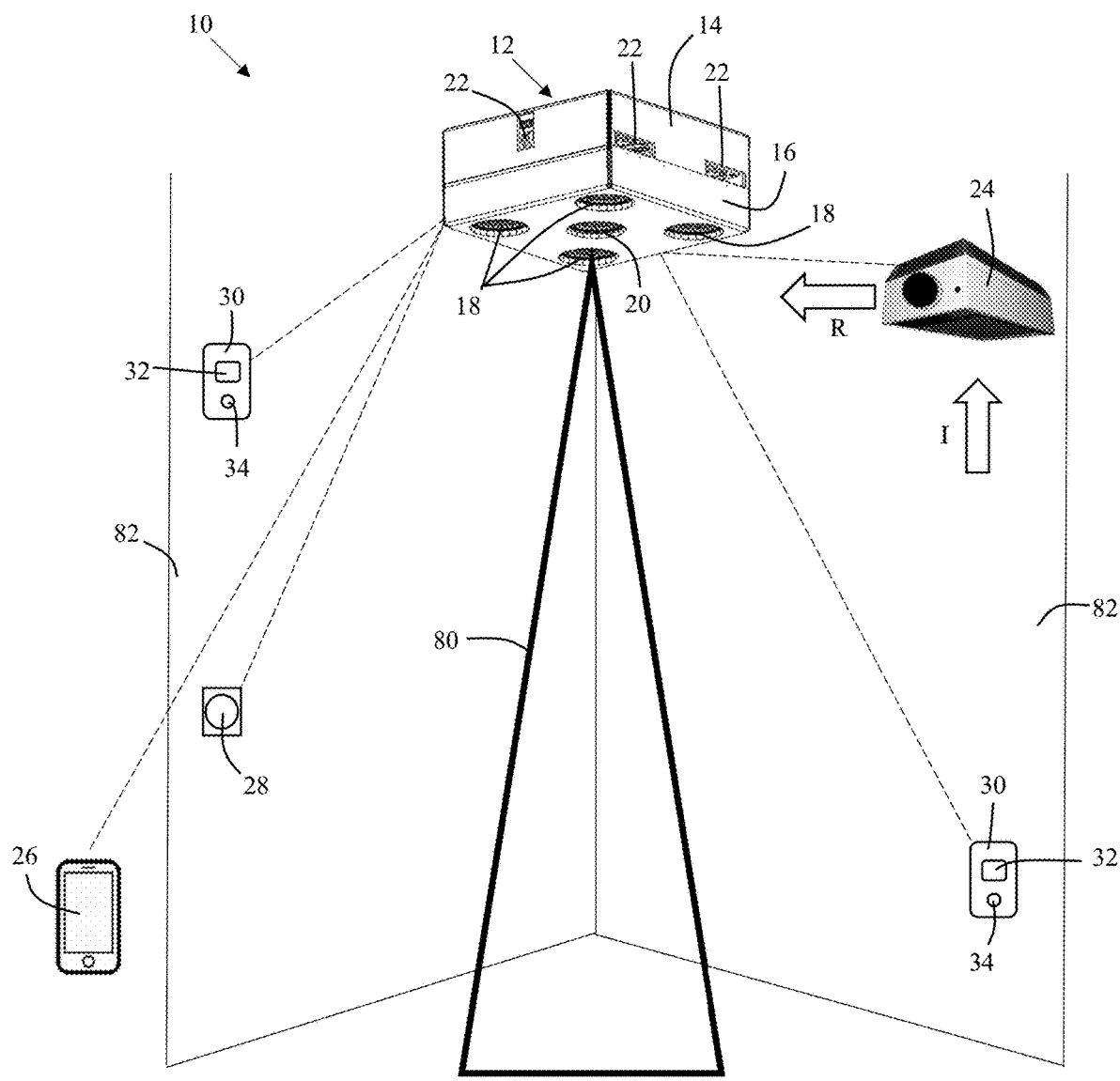
FIG. 1 is a perspective view of a sterilizing system.

The explanations and illustrations presented herein are intended to acquaint others skilled in the art with the invention, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present teachings generally relate to a sterilizing system. The sterilizing system may function to sterilize a desired area or room. Sterilizing as used herein may be defined as killing all bacteria, germs, spores, mold, fungi, pathogens, viruses, pollen, fumes, volatile organic compounds (VOCs), or a combination thereof. The sterilizing may be completed by damaging a virus or other pathogen— such as by damaging a nucleus or make-up of a virus or other pathogen—thereby distinguishing the virus or other pathogen and eliminating the risk of contamination for any person present in the vicinity or in contact with a previously contaminated surface.

The sterilizing system may sterilize a designated area or room based upon positioning of devices within the sterilizing system. As such, the sterilizing system may provide a whole-room or whole-building sterilizing means. Thus, the sterilizing system may sterilize surfaces, a designated area, items, other contaminated objects, or a combination thereof. Similarly, the sterilizing system may advantageously be implemented to sterilize a fluid, such as water, air, other substances, or a combination thereof.

The sterilizing system may include one or more devices. The one or more devices may include a light sterilizer, an air sterilizer, a sensor, a mobile device, or a combination thereof. It is envisioned that some or all the devices within the sterilizing system may be in wired or wireless communication with one another to create a robust system. For example, all of the devices may be in one-way or two-way communication with each other to properly communicate any status changes to the sterilizing system.

It is also envisioned that the sterilizing system may be adjustable based on a desired application. For example, the sterilizing system may be scaled based upon an area requiring sterilizer. The larger the area, the greater number of devices (e.g., light sterilizers, sensors, air sterilizer, etc.) that may be implemented to effectively sterilize the area. Thus, the sterilizing system may advantageously provide a highly customizable solution to sterilizing needs.

The sterilizing system may beneficially sterilize a desired area free of physical interaction from a user. Utilizing the devices of the sterilizing system, such as the light sterilizer and/or air sterilizer, the sterilizing system may sterilize any surfaces, objects, and air in a designated area or room in a contactless manner. The sterilizing system may run a sterilizing cycle based upon a manual start command sent by a user (e.g., through a mobile device app) or may automatically run the sterilizing cycle. For example, the sterilizing system may be scheduled to run at designated times or may automatically run a sterilizing cycle once the sensors of the sterilizing system no longer detect the present of any people with the designated area or room.

Beneficially, the robust devices of the sterilizing system may provide a variety of safety mechanisms to prevent exposure of any person to the UVC light. To provide such safety, the sterilizing system may include one or more room sensors in communication with any other devices of the sterilizing system, such as the light sanitizer. The sensors may include a radar sensor, infrared (IR) sensor, other position or thermal sensor, or a combination thereof. As a result, the sensors may monitor the presence of any person within the designated area or room. If a user is detected, the light sterilizer may be prevented from turning on, thereby preventing any present person from being exposed to the light. To create such monitoring, the room sensors can be positioned anywhere within or near the designated area or room (e.g., walls, ceilings, floors, doors, windows, etc.).

Similarly, the sterilizing system may also include an emergency stop to allow for manual interaction between a user and the sterilizing system. If a user must urgently stop a sterilizing cycle of the system, the emergency stop may be triggered, thereby immediately shutting down the system. The emergency stop may be positioned in an area within the designated area or room that allows for easy interaction by a user. For example, the emergency stop may be located on a wall near an entrance or exit of the room. The emergency stop may be any button, trigger, switch, or other interactive toggle that allow for communication (wired or wirelessly) between the emergency stop and devices within the sterilizing system.

The sterilizing system may also be operated by a mobile device. The mobile device may be any device that communicates with the sterilizing system remotely, such as a mobile phone, table, computer, remote, or a combination thereof. The mobile device may communicate with the devices within the sterilizing system wirelessly, such as via Bluetooth, Wi-Fi, or other wireless means. Thus, a mobile device may function as an interface of the sterilizing system for a user.

The interface on the mobile device may include an application or other software to allow for customization and configuration of the sterilizing system via the mobile device. One or more commands or settings may be adjusted via the application, such as sterilizing schedules, intensity of the light sterilizer, cycling on and/or off the sterilizing system, emergency shutoff, diagnostics mode, movement of the light sterilizer and or other devices within the sterilizing system, or a combination thereof.

The sterilizing system may include a light sterilizer. The light sterilizer may function to sterilize a desired area or room using one or more lights. The sterilizing may sterilize surfaces, objects, air, or a combination thereof in the desire area or room. The light sterilizer may be mobile or may remain stationary during operation. The light sterilizer may be adjustable—such as by adjusting a tilt, position, angle, or a combination thereof—or may be fixed. Beneficially, it is envisioned that the light sterilizer may be integrated into one or more devices or existing system. Such existing systems and/or devices may include: a heating, ventilation, and air conditioning (HVAC) system within a residential building, commercial building, or vehicle; vehicles such as airplanes, automobiles, subway transit systems, boats, or a combination thereof; production lines for one or more commercial industries; retail businesses; other devices or existing systems; or a combination thereof. For example, the light sterilizer may be integrated into a vent or duct of a home HVAC system to sterilize an airflow traveling through the duct.

The light sterilizer may include one or more ultraviolet (UV) lights. In particular, the UV lights may be UV-C lights that more effectively sterilize an environment from bacteria, viruses, fungi, spores, mold, pollen, fumes, VOCs, other pathogens, or a combination thereof. The UV-C light may be an invisible light to the naked eye, ranging from a wavelength of about 100 nm to about 280 nm. However, tuning of the UV-C lights within the light sterilizer may be completed based on a given application. The number of UV-C lights within each light sterilizer may also vary. For example, the light sterilizer may include one or more, two or more, or three or more UV-C lights. The light sterilizer may include ten or less, eight or less, or six or less UV-C lights. Additionally, the UV-C lights may be bonded together or separate to create one or more sterilizing zones. For example, one or more chip on board (COB) UV-C lights may be implemented into the light sterilizer to create groups or bunches of UV-C lights at designated locations along the light sterilizer. As such, the light sterilizer may beneficially provide additional and increased UV-C exposure for the designated area or room.

It should be noted that while UV-C lights may be utilized in the light sterilizer, UV-B lights might also be implemented for certain applications. UV-B lights may beneficially allow for sterilizing of a desired area or room at a decreased rate with a wavelength that is less harmful to any person present in the sterilizing zone of the light. UV-B lights may range from a wavelength of about 280 nm to about 315 nm. Thus, it is envisioned that the light sterilizer may be tunable to alternate or utilize both UV-C and UV-B lights. For example, UV-B lights may be turned while a person is present in the room for a length of time. When the person exits the room, the light sterilizer may switch to UV-C lights to sterilize the room more efficiently. This switching may be done automatically within the system or manually via a user.

While UV-C and UV-B lights have been described above, it is envisioned that various light wavelengths may be implemented into the devices described herein. For example, while UV-C light may be designated for a range of about 100 nm to about 280 nm, the device may facilitate using a UV light within a range of about 100 nm to about 400 nm. For example, the light sterilizer may utilize Far UV light, which may be in the range of about 200 nm to about 300 nm, thereby providing a light range safer for exposure to human. Additionally, it should also be noted that UV-C, UV-B lights, and Far UV may be primarily used in the light sterilizer, UV-A light in the range of about 300 nm to about 400 nm and Near UV light (black light) in the range of about 300 nm to about 400 nm may also be utilized even further customize the light sterilizer for a necessary application. Thus, it may be gleaned from the present teachings that the UV lights described herein may vary and/or be highly tunable or adjustable to provide a robust system for sterilization. Additionally, the ability to tune or adjust such UV lights may also facilitate secondary functionality of the system, such as providing a work light, a black light, lights safer for human exposure, accent lighting, decor lighting, or a combination thereof.

The UV lights within the light sterilizer may be interchangeable. Additionally, the UV lights may also be easily replaceable and accessible for maintenance and/or replacement. Thus, the light sterilizer is beneficially even further customizable by providing a means for quick adjustment of one or more UV lights within the light sterilizer.

The light sterilizer may also include an LED light. The LED light may function to indicate a status of the light sterilizer, such as "cycle ON," "cycle OFF," if a failure exists, if the light sterilizer is powered on and/or off, diagnostics mode, or a combination thereof. The LED light may utilize one or more colors, such as red, green, blue, yellow, or a combination thereof, to indicate different statuses. As such, the LED light may be positioned along the light sterilizer to ensure a user or person near the light sterilizer may see the LED light.

The LED light, the UVC lights, or both may be secured to a light printed circuit board assembly (PCBA). The LED light, the UVC lights, or both may be integrated into the light PCBA free of any mechanical fasteners. The light PCBA may control operation of the LED light, the UV-C light, or both. The light PCBA may include one or more transistors, one or more capacitors, one or more processors, one or more storage devices, one or more transmitters, one or more receivers, one or more memory devices, or a combination thereof. As such, it is envisioned that the light PCBA may communicate with one or more devices, such as the mobile device of the sterilizing system, to receive and/or send data.

The lights and/or the light PCBA may be positioned within a housing of the light sterilizer. The housing may at least partially or even fully enclose the lights and/or the light PCBA. However, it is envisioned that the housing may include one or more cutouts for the UV-C lights to create a sterilizing zone (i.e., an area of sterilizing created by the UV-C lights). The housing may be a single piece or may be interconnected pieces. As such, the housing may include an upper housing and a lower housing connected via fasteners, interlocking, adhesives, or a combination thereof. The housing may include one or more vents, one or more slots, one or more cutouts, or a combination thereof.

Reflectors may be secured to the housing. The reflectors may function to direct and/or reflect light emitted from the UV-C lights, the LED light, or both. The reflectors may aid in creating a sanitizing zone of the UV-C lights. Thus, each UV-C light may be located within a separate reflector, or more than one UV-C light may be positioned within a single reflector. The reflectors may be flexible, tiltable, or otherwise adjustable to direct the lights in a desired direction. Alternatively, the reflectors may be fixed to the housing and remain substantially stationary.

While the light sterilizer may remain stationary and may be mounted within a room or designated area, it also envisioned that the light sterilizer may also be movable. More specifically, the light sterilizer may include one or more components that facilitate movement of the light sterilizer within a desired area or room. For example, the light sterilizer may include some or all the mechanics of an autonomous drone to allow for movement within a desired area. Alternatively, the light sterilizer may be connected to a track or cable system for movement within a designated area or room. The track or cable system may be mounted within the designated area or room to provide a path of movement for the light sterilizer. As such, one or more tracks and/or cables may be interconnected to provide a desired path.

To move along such a track or cable system, the light sterilizer may include a driver. The driver may function to move the light sterilizer along the track or cable system. The driver may be powered and/or articulated by a drive motor integrated into or otherwise connected to the driver. The drive motor may be any motor, such as a brushed DC or brushless DC motor, AC motor, or a combination thereof. Based upon articulation of the drive motor, the driver may engage the track or cable system and move the light sterilizer.

The path of movement of the light sterilizer may be controlled via a trolley driver printed circuit board assembly (PCBA). The trolley drive PCBA may be in communication with the mobile device or another device within the sterilizing system so that a user may control movement of the light sterilizer. Similarly, a planned path of movement may be programmed into the trolley driver PCBA to dictate movement of the light sterilizer.

One or more position sensors may also be located along the light sterilizer. The position sensors may be located within the housing or on the outside of the housing. The position sensors may monitor a position of the light sterilizer to ensure proper movement along the track or trolley system. For example, the position sensors may prevent the light sterilizer from hitting walls or endpoints along the track or cable system. Therefore, the position sensors may be located near or adjacent to the track or cable system path.

The driver may drive the light sterilizer so that the light sterilizer is guided along one or more trolleys that engage the track or cable system. The trolleys may contain a bearing, a bushing, or both, that allows for decreased friction between the trolleys and the light sterilizer during movement. Thus, the driver may require less force or output to move the light sterilizer. The trolleys may be located outside the housing of the light sterilizer or may be positioned within the housing. If positioned within the housing, the housing may include one or more slots so that the track or cable system may extend through the housing and engage the trolleys. For example, the track may extend through the housing so that one or more bearings of the trolleys rest along or otherwise engage a lip of a track or a cable of a cable system.

To ensure proper engagement between the trolleys, the driver, or both and the track or cable system, the light sterilizer may include a biasing member. The biasing member may engage the track or cable system and bias the trolleys and/or drive against the track or cable system. As a result, the biasing member may substantially prevent slippage between the trolley and/or the driver and the track or cable system. The biasing member may include a spring or other elastic member to create a biasing force against the track or cable system. The biasing member may engage any surface of the track or cable system to maintain connection between the trolleys and/or driver and the track or cable system. The biasing member may include an arm or bracket that connects the biasing member to the light sterilizer so that a biasing portion may extend into and engage the track or cable system.

The biasing member may engage a spacer of the track. The spacer may function to decrease a distance between the biasing member and the track to ensure the biasing member imparts a biasing force against the track. The spacer may be positioned anywhere along the track, such as between one or more lips that form a channel along the spacer. The spacer may extend along an entire length of the track or may be positioned in localized regions of the track. Similarly, a plurality of spacers may be located within a single slot or channel of the track, within a plurality of slots or channels of the track, or both, to communicate with one or more biasing member of the light sterilizer.

The light sterilizer may also include a thermal management system. The thermal management system may function to maintain a temperature of the light sterilizer during operation. The thermal management system may prevent overheating of the light sterilizer due to the heat expelled from the UV-C lights during cycling. Thus, the thermal management system may be interconnected or in communication with the UV-C lights to prevent overheating that may cause damage to the light sterilizer or may otherwise render the light sterilizer inoperable. While exemplary components of a thermal management system are described herein, it is envisioned that alternatives may exist. For example, the thermal management system may include one or more water-coolant systems to cool the UV-C lights.

The thermal management system may include a heat sink. The heat sink may be connected to or in contact with the UV-C light to transfer heat created by the UV-C light. For example, a first surface may contact the UV-C light to retain or draw heat from the UV-C light and transfer such heat to an opposing second surface of the heat sink. As a result, the UV-C light may maintain an acceptable operating temperature without risk of failure. Each UV-C light may be connected to a heat sink or some UV-C lights may share a heat sink. For example, one heat sink may contact all UV-C lights within the light sterilizer.

The heat sinks may also be connected to a fan. The fan may function to cool the heat sinks, further remove and/or circulate heat being expelled from the UV-C lights, or both. The fan may be located within the housing of the light sterilizer or outside of the light sterilizer. Separate fans may be connected to each individual heat sink or a single fan may be utilized. Additionally, the fans, the heat sink, or both may be positioned near slots on the housing to expel the heat from the housing of the light sterilizer.

In addition to the light sterilizer, the sterilizing system may include an air sterilizer. The air sterilizer may function circulate and sterilize an airflow within a desired area or room. The air sterilizer may be used on conjunction with the light sterilizer to further ensure sterilization of the desired area or room. The air sterilizer may be mounted separated from the light sterilizer or may be connected to the light sterilizer. As such, the air sterilizer may move with the light sterilizer along the track or cable system if desired. However, the air sterilizer may also operate independently of the light sterilizer and may be mounted to a wall or ceiling or a room for operation. It is envisioned that air within the desired area or room may circulate through the air sterilizer.

To sterilize the air, the air sterilizer may include an intake. The intake may function to receive air from the designated area or room and move the air through the air sterilizer. The intake may be an opening or vent of a housing of the air sterilizer. To help facilitate movement of the air through the air sterilizer, a fan may be located within the air sterilizer. An impeller of the fan may intake the air and push it through a sterilizing device within the air sterilizer, such as a UV-C light.

Once the air is circulated into the air sterilizer and sterilized, the air may be expelled via an outlet or duct. The duct may direct an output path of the sterilized air in any direction. For example, the duct may be flexible, extendable, retractable, or a combination thereof to direct the air. Beneficially, the duct may expel the sterilized air away from the intake to ensure optimized circulation of clean air within the designated area or room.

Turning now to the figures, FIG. 1 illustrates a perspective view of a sterilizing system 10. The sterilizing system 10 may be configured to sterilize one or more locations or areas using one or more devices within the sterilizing system 10. FIG. 1 illustrates an exemplary room (or portion of a room) that may be sterilized using the sterilizing system 10 described herein.

The sterilizing system 10 may include a light sterilizer 12. As shown, the light sterilizer 12 may be mounted along an upper portion of one or more walls 82 or may be mounted on a ceiling of a room. The light sterilizer 12 may include one or more Ultraviolet-C (UVC) lights 18 that may cast a sterilizing zone 80 within the room. It is envisioned that the UVC lights 18 may be turned on to sterilize a portion of the room that falls within the sterilizing zone 80. The light sterilizer 12 may include any desired number of UVC lights 18 to ensure proper sterilizing of a desired area. For example, a larger number of UVC lights 18 may be utilized to create a larger sterilizing zone 80, thereby sterilizing a greater area of a room. Beneficially, the UVC lights 18 may sterilize a room or an area by killing all germs, spores, mold, pathogens, viruses, other contaminants, or a combination thereof. For example, the UVC lights 18 may break the molecules of a virus, thereby killing the virus and eliminating the risk of illness for any person present in the room and/or area after sterilizing.

The light sterilizer 12 may also include an LED light 20. The LED light 20 may be positioned anywhere along the light sterilizer 12. However, the LED light 20 may beneficially be positioned in a visible location along the light sterilizer 12 to ensure people entering the room may easily see the LED light 20. The LED light 20 may visually project one or more colors to indicate a present status of the light sterilizer 12. For example, the LED light 20 may flash green to indicate that the light sterilizer 12 is starting a cycle, may flash red to indicate that the light sterilizer 12 is stopping a cycle, may illuminate or flash blue during a cleaning cycle (i.e., when the UVC lights 18 are turned on), or a combination thereof. It should be noted that the LED light 20 may be programmed using a light printed circuit board assembly (PCBA) to flash or illuminate for any desired status or designation, such as those indicated above or other statuses, such as a test or demonstration mode, an error mode, or both.

The UVC lights 18 and the LED light 20 may be at least partially encapsulated in an upper housing 14, a lower housing 16, or both of the light sterilizer 12 that substantially enclose the inner components of the light sterilizer 12. The upper housing 14, the lower housing 16, or both may include one or more slots 22. The slots 22 may function to receive a component that connects to the light sterilizer 12, may provide ventilation to the light sterilizer 12, or both.

The light sterilizer 12 may be utilized as a single-device system. Accordingly, it is envisioned that the light sterilizer 12 may be installed within a room or area for sterilizing without any further devices for sterilizing purposes. Thus, it may be gleaned that the present teachings beneficially provide a sterilizing system 10 with a high level of customization and tunability.

While the light sterilizer 12 may be utilized independently of any further devices, the sterilizing system 10 may also include an air sterilizer 24. The air sterilizer 24 may be configured to circulate air within the room or a designated air and purify said air. The air sterilizer 24 may include a sterilizing element within a housing of the air sterilizer 24, such as one or more UVC lights, that sanitizes the air passing through the air sterilizer 24. As shown in FIG. 1, the air sterilizer 24 may have an intake portion that intakes air in the direction (I). After the air enters the air sterilizer 24 and is sanitized, the air may exit an outlet duct in the direction (R) and reenter the room. The air sterilizer 24 may be positioned anywhere within the room or a desired area. For example, the air sterilizer 24 may be mounted to a wall 82 or ceiling to optimally circulate the air. The air sterilizer 24 may beneficially be positioned within an area outside of the sterilizing zone 80 of the light sterilizer 12 to sterilize the room or desired area even further. It should be noted that the air sterilizer 24 may also be positioned within the sterilizing zone 80 and have some overlap in sterilizing with the light sterilizer 12.

The light sterilizer 12, air sterilizer 24, or both may be in wired and/or wireless electronic communication with one or more room sensors 30. The room sensors 30 may be strategically positioned within a room or desired area to detect the presence of a person. For optimal coverage of the room or desired area, the room sensors 30 may be mounted along the walls 82 and/or ceiling to ensure any person entering the room or desired area is quickly detected. For detection, the room sensors 30 may include a radar sensor 32, infrared (IR) sensor 34, or both. The radar sensor 32 and the IR sensor 34 may immediately detect the presence of a person in the room. As such, the room sensors 30 may advantageously provide a safety mechanism to the sterilizing system 10. For example, if a person is detected by the room sensors 30, the sterilizing system 10 may prevent activation of a sterilizing cycle to ensure the person present in the room or designated area is not exposed to the UVC lights 18. Similarly, if a sterilizing cycle is currently running and a person enters the room, the room sensors 30 may detect the person and immediately terminate the sterilizing cycle until the person exits the room or designated area.

To ensure safety even further for any person entering or present in the room, the sterilizing system 10 may include an emergency stop 28. The emergency stop 28 may be a button positioned in an accessible location within the room to ensure that a user may manually trigger the emergency stop 28 to immediately stop a sterilizing cycle. The emergency stop 28 may be any switch, button, toggle, touch plate, or a combination thereof that a user physically contacts to stop a cycle of the sterilizing system 10. The emergency stop 28 may also be wired directly to the light sterilizer 12 or may be in wireless communication to transmit a "stop" command to the light sterilizer 12.

To provide such robust safety, the room sensors 30, the light sterilizer 12, and the air sterilizer 24 may be in wired or wireless communication with one another. It should also be noted that the room sensors 30 may be in communication with only the light sterilizer 12 or the air sterilizer 24, or the room sensors 30 may be in communication with both the light sterilizer 12 and the air sterilizer 24. The communication between the room sensors 30 and the light sterilizer and/or the air sterilizer 24 may be one-way communication or two-way communication. As such, any of the devices described herein may include a receiver, a transmitter, or both to ensure proper communication.

Additionally, it is envisioned that any number of room sensors 30 may be utilized based on a given application. For example, a larger room may require an increased number of room sensors 30 properly monitor the room. As such, one or more room sensors 30, five or more room sensors 30, or ten or more room sensors 30 may be used. Similarly, 30 or less room sensors 30, 20 or less room sensors 30 or 15 or less room sensors 30 may be used for a given application.

The sterilizing system 10 may be controlled via a remote mobile device 26. The mobile device 26 may be a mobile phone, tablet, computer, wireless remote, or a combination thereof. Beneficially, the mobile device 26 may provide a user the ability to start and/or stop cycles of the sterilizing system 10 wirelessly without physically interacting with the devices. It is also envisioned that the mobile device 26 may include an application for the sterilizing system 10, thereby providing the user further programming ability. For example, the application for the sterilizing system 10 may allow for a user to schedule sterilizing times throughout a day, adjust intensity of the UVC lights 18, the LED light 20, or both, adjust movement speed of the light sterilizer 12, adjust fan speed of the air sterilizer 24, further tune movement of the air sterilizer 24 and/or the light sterilizer 12, or a combination thereof. To facilitate such interaction between a user and the sterilizing system 10, the mobile device 26 may be in one-way or two-way communication with the room sensors 30, the air sterilizer 24, the light sterilizer 12, or a combination thereof. The communication between the remote mobile device 26 and the sanitizing system 10 may be via an application (i.e., an "app"), wireless communication such as Wi-Fi or Bluetooth, or a combination thereof.

Figure 2:
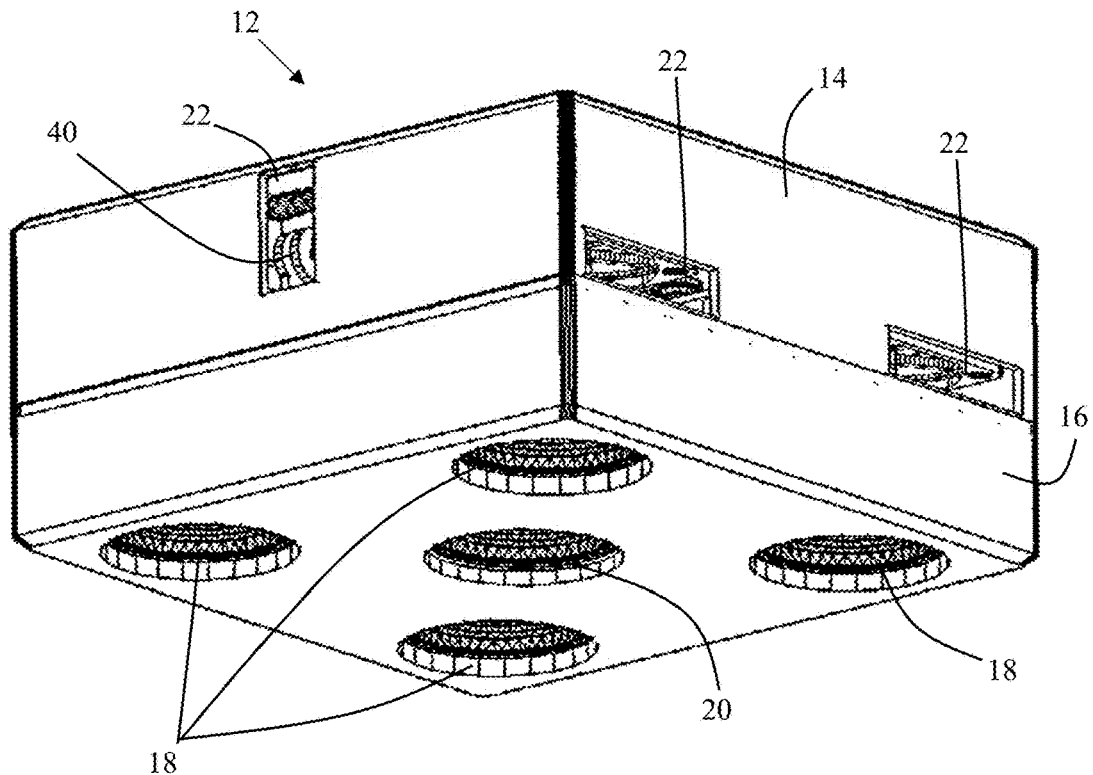
FIG. 2 is a perspective view of a light sterilizer.

FIG. 2 illustrates a perspective view of a light sterilizer 12. The light sterilizer may include an upper housing 14 connected to a lower housing 16 to substantially encapsulate the inner components of the light sterilizer. The upper housing 14 and the lower housing 16 may be connected via one or more fasteners, one or more mechanical interlocks, one or more adhesives, or a combination thereof. It is also envisioned that the upper housing 14 and the lower housing 16 may be integrally formed with one another (i.e., a clamshell design). The upper housing 14 and/or the lower housing 16 may include one or more slots 22 that extend into an inner compartment of the light sterilizer 12. The slots 22 may allow for engagement between trolleys 40 of the light sterilizer 12 and a track or cable system, thereby facilitating movement of the air sterilizer 12 within a room or designated area along the track or cable system (see FIGS. 4 and 7). The slots 22 may also provide ventilation for the light sterilizer 12 to prevent potential overheating caused by operation.

As shown, the light sterilizer 12 may include a plurality of Ultraviolet-C (UVC) lights 18 positioned near holes in the lower housing 16. The UVC lights 18 may beneficially project light into a desired area or room to sterilize the air and any surfaces within a sterilizing zone defined by the UVC light 18 projection (see FIG. 1). While four UVC lights 18 are shown, the light sterilizer 12 may include any desired number of UVC lights based upon a given application.

In addition to the UVC lights 18, the light sterilizer 12 may also include an LED light 20 to indicate a status of the light sterilizer, such a "sterilizing cycle start", "sterilizing cycle stop", "cleaning cycle on", "error", "demonstration mode", or a combination thereof. The LED light 20 may provide a color-designation for desired statuses, such as red, green, blue, or a combination thereof. Additionally, the LED light 20 may be programmed to flash or synchronize operation with an audible indication from the light sterilizer 12, such as a beep or chime.

Figure 3:
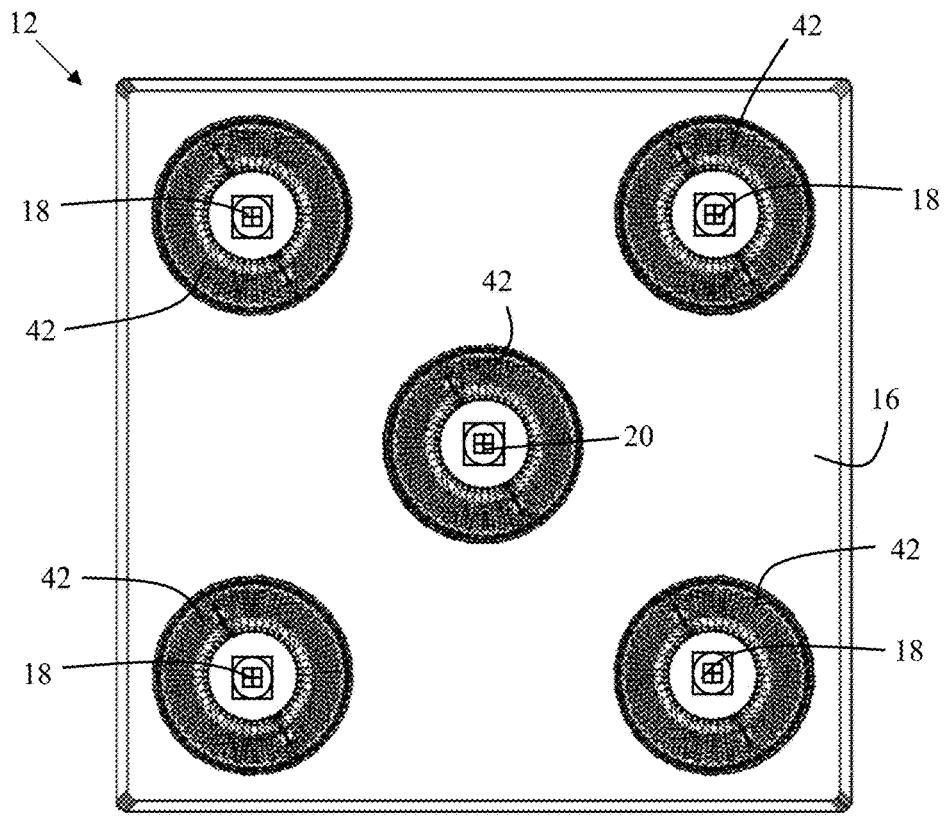
FIG. 3 is a bottom view of a light sterilizer.

FIG. 3 illustrates a bottom view of the light sterilizer 12 of FIG. 2. As shown, the UVC lights 18 and the LED light 20 may be enclosed within the lower housing 16 of the air sterilizer 12. To ensure proper projection of the light within a room or desired area, the UVC lights 18 and the LED light 20 may be positioned within reflectors 42 secured around a periphery of cutouts within the lower housing 16. The UVC lights 18 and the LED light 20 may be centrally positioned within the reflectors 42 to evenly distribute the projected light within the room or desired area. For example, the UVC lights 18 and/or the LED light 20 may be coaxial with an axis of the reflectors 42. However, it envisioned that the position of the lights relative to the reflectors 42 may be adjustable. Similarly, while the reflectors 42 shown herein are substantially conical, any shape may be utilized. Additionally, the reflectors 42 may be moveable—tiltable, rotatable, extendable, etc.—to finely tune a direction the light from the UVC lights 18 and/or the LED light 20 may project.

Figure 4:
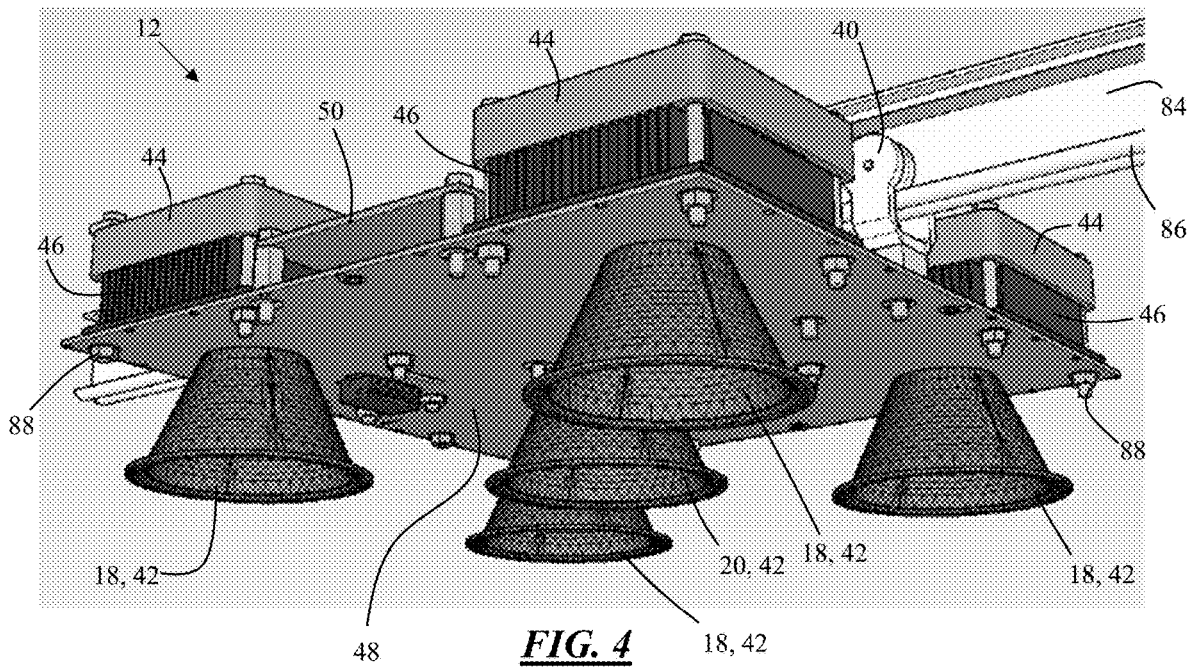
FIG. 4 is a perspective view of a light sterilizer with the housing removed.

FIG. 4 illustrates a perspective view of a light sterilizer 12 with the housing removed for simplicity. The light sterilizer 12 may include a plurality of Ultraviolet-C (UVC) lights 18 and an LED light 20 positioned within reflectors 42. The reflectors 42 may be mounted to a housing of the light sterilizer 12, such as the lower housing as shown in FIG. 2. However, the reflectors 42 may also be fixed to any other components of the light sterilizer, such as a light PCBA 48. The light PCBA 48 may be configured to control the UVC lights 18, the LED light 20, or both. The light PCBA 48 may include one or more electrical components to ensure proper operation of the UVC lights 18 and the LED light 20, such as one or more receives, one or more capacitors, one or more processors, one or more transistors, one or more receivers, one or more microchips, one or more sensors, or a combination thereof. For example, the light PCBA 48 may include one or more temperature sensors to monitor a temperature of the light sterilizer 12 during operation and shut down the light sterilizer 12 when at risk of overheating. It is envisioned that the light PCBA 48 may operate the UVC lights 18 and the LED light 20 but may also tune or adjust such operation. Tuning may include adjusting the intensity of the UVC lights 18, programming operation of the UVC lights 18 and the LED light 20, or both.

The light sterilizer 12 may also include one or more thermal management system. The thermal management system of the light sterilizer 12 may include a heat sink 46 abutting each of the UVC lights 18. The heat sinks 46 may help decrease a temperature of the UVC lights 18 during operation by transferring the heat created by the UVC lights 18 through the heat sinks 46, whereby fans 44 connected to the heat sinks 46 may propel the heat away from the device. For example, the air may be pushed out of the one or more slots within the housing of the light sterilizer 12 via the fans 44. Furthermore, as shown, the heat sinks 46, the fans 44, or both may be directly or indirectly mounted to the light PCBA 48 by one or more fasteners 88.

The light sterilizer 12 may also include one or more trolleys 40. The trolleys 40 may engage a track 84 mounted within a room to allow the light sterilizer 12 to move along the track 84. Beneficially, the light sterilizer 12 may then sterilizer a greater coverage area when compared to remaining stationary in a single spot. To facilitate such movement, the light sterilizer 12 may also include driver that drives the light sterilizer 12 along the track 84 (see FIG. 6). The driver may be controlled via a trolley driver PCBA 50 mounted to the light PCBA 48.

It should also be noted that while a track 84 is describe herein, the one or more trolleys 40 may also engage one or more cables within a cable system for movement of the light sterilizer 12. The one or more cables may be suspended across all or a portion of a room to allow for movement. The one or more cables may be mounted to a ceiling, walls, mounting structures, or a combination thereof to create a cable system for movement of the light sterilizer 12. Similarly, the light sterilizer 12 may be guided or otherwise moved by additional means other than a track 84 or a cable system. For example, the light sterilizer 12 may include one or more wheels or other mobility means to move the light sterilizer 12 along a floor, one or more walls, a ceiling, another structure, or a combination thereof. As such, it is envisioned that the light sterilizer 12 may be configured for a variety of movement means, as thus may provide a sterilization solution for various applications.

Figure 5:
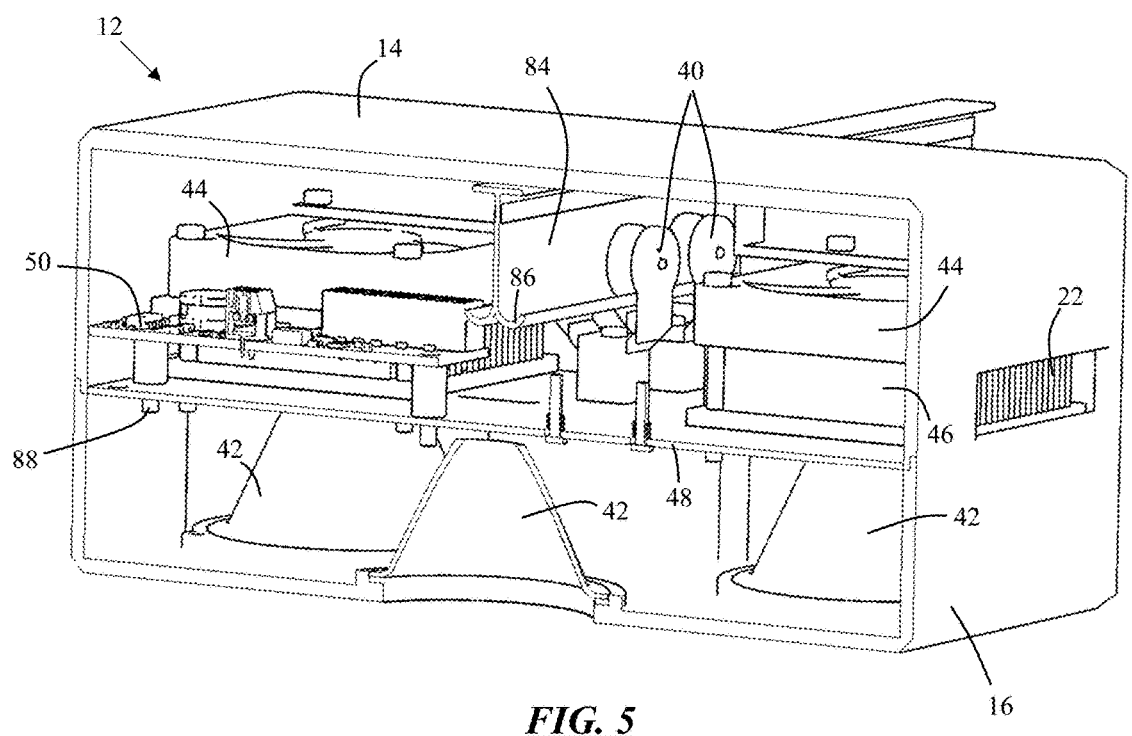
FIG. 5 is a cross-section of a light sterilizer.

FIG. 5 illustrates a cross-section of a light sterilizer 12. The light sterilizer 12 includes an upper housing 14 and a lower housing 16 interconnected to form a cavity within the housings. The light sterilizer 12 may include a plurality of UVC lights and an LED light positioned within reflectors 42. The reflectors 42 may be mounted to a light printed circuit board assembly (PCBA) 48 that controls the UVC lights, the LED light, or both. The light sterilizer 12 may also include a heat sink 46 abutting each of the UVC lights positioned within the reflectors 42. The heat sinks 46 may help decrease a temperature of the UVC lights during operation by transferring the heat created by the UVC lights through the heat sinks 46, whereby fans 44 connected to the heat sinks 46 may propel the heat away from the device. For example, the air may be pushed out of the one or more slots 22 within the housing of the light sterilizer 12 via the fans 44. Furthermore, as shown, the heat sinks 46, the fans 44, or both may be directly or indirectly mounted to the light PCBA 48 by one or more fasteners 88.

The light sterilizer 12 may also include a plurality of trolleys 40. The trolleys 40 may engage a track 84 mounted within a room to allow the light sterilizer 12 to move along the track 84. The trolleys 40 may engage a lip 86 along the track so that the trolleys 40 remain connected to the track 84 during movement. The lip 86 may be any shape to engage the trolleys 40. Beneficially, the light sterilizer 12 may then sterilize a greater coverage area when compared to remaining stationary in a single spot. To facilitate such movement, the light sterilizer 12 may also include driver that drives the light sterilizer 12 along the track 84 (see FIG. 6). The driver may be controlled via a trolley driver PCBA 50 located adjacent to the light PCBA 48. The trolley driver PCBA 50 and the light PCBA 48 may be connected to each other or may be located anywhere within the light sterilizer 12.

It is also envisioned that the driver may be controlled via the track 84 or a cable system. For example, the driver may be connected to an electrically energized track 84 or cable system, a standalone power source, or both that controls the driver and facilitates movement of the light sterilizer 12.

Figure 6:
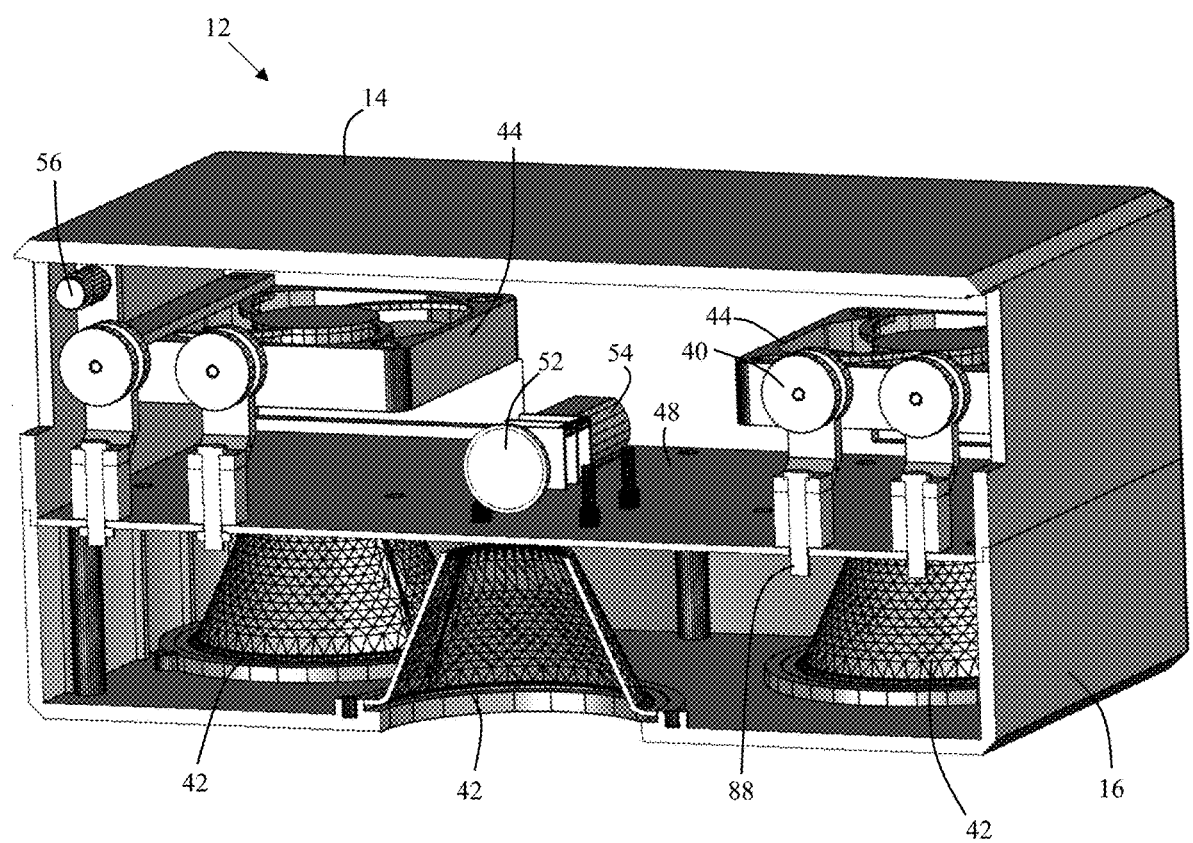
FIG. 6 is a cross-section of a light sterilizer.

FIG. 6 illustrates another cross-section of a light sterilizer 12. The light sterilizer 12 includes an upper housing 14 and a lower housing 16 interconnected to form a cavity within the housings. The light sterilizer 12 may include a plurality of UVC lights and an LED light positioned within reflectors 42. The reflectors 42 may be mounted to a light printed circuit board assembly (PCBA) 48 that controls the UVC lights, the LED light, or both. However, the reflectors 42 may also be mounted to the lower housing 16 around a circumference of each opening for the UVC lights and the LED lights. The light sterilizer 12 may also include a heat sink (not shown) abutting each of the UVC lights positioned within the reflectors 42. The heat sinks may help decrease a temperature of the UVC lights during operation by transferring the heat created by the UVC lights through the heat sinks, whereby fans 44 connected to the heat sinks 46 may propel the heat away from the device.

The light sterilizer 12 may also include a plurality of trolleys 40 secured to the light PCBA 48 via one or more fasteners 88. The trolleys 40 may engage a track or cable system mounted within a room to allow the light sterilizer 12 to move along the track or cable (see FIG. 5). To facilitate such movement, the light sterilizer 12 may also include driver 52 that drives the light sterilizer 12 along the track or cable system. The driver 52 may include a drive motor 54 controlled via a trolley driver PCBA (not shown) so that the drive motor 54 rotates the driver 52, whereby the driver 52 engages the track or cable system and moves the light sterilizer 12 along the track or cable system. Additionally, to ensure consistent engagement between the trolleys 40, the driver 52, or both and the track or cable system, the light sterilizer 12 may also include a biasing member 56 to bias the trolleys 40 and/or the drive 52 against the track or a lip of the track, or the cable system.

While a driving system of the light sterilizer 12 is describe herein, it should also be noted that the light sterilizer may also be free of such a driving system. For example, the light sterilizer 12 may be free of a driver 52, trolleys 40, or both. Advantageously, this may allow for a lighter and more cost-effective sterilizer if an application does not require movement of the light sterilizer 12 once installed. As such, the light sterilizer 12 may be customized based on a given application.

Figure 7:
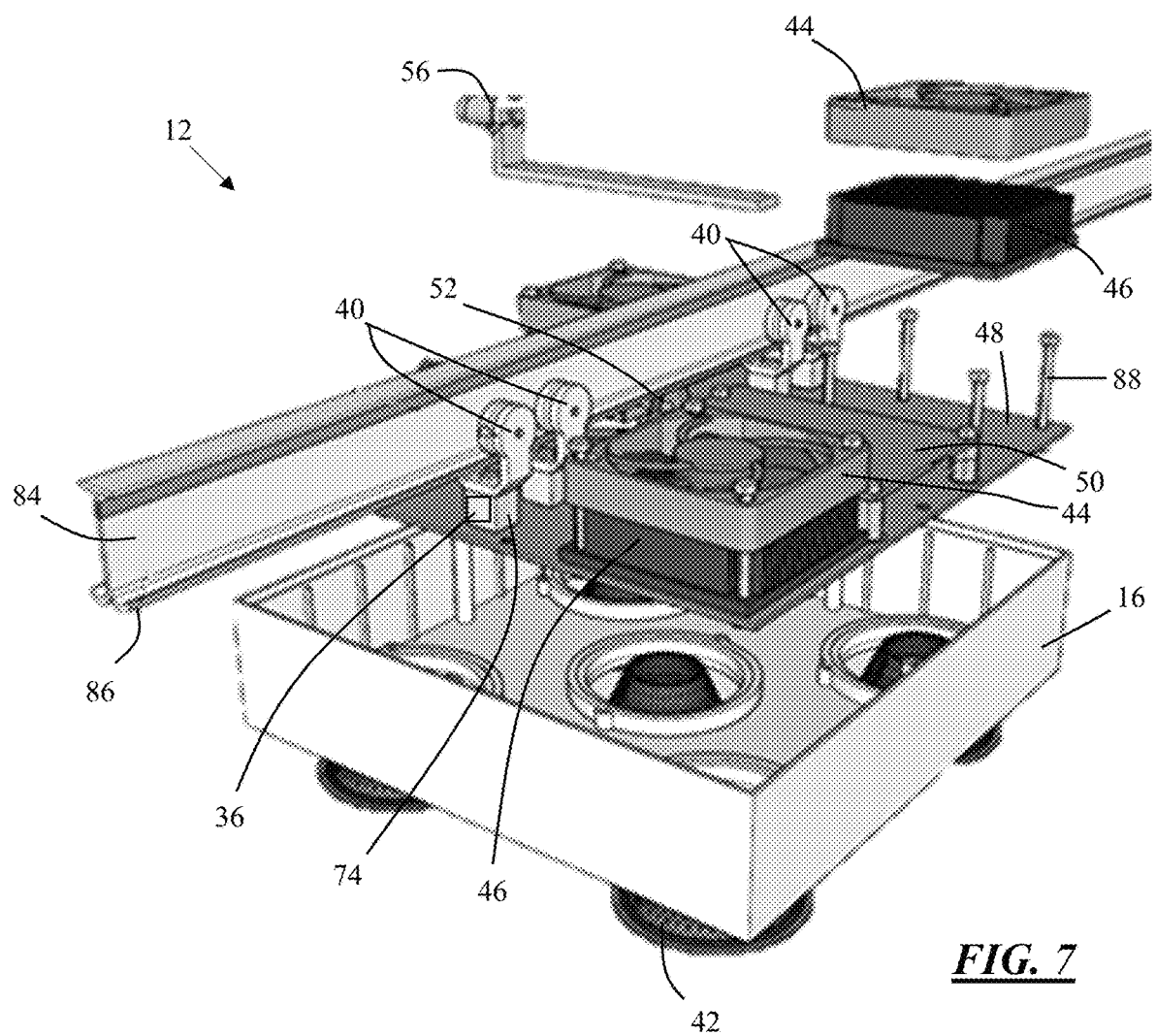
FIG. 7 is an exploded view of a light sterilizer.

FIG. 7 illustrates an exploded view of a light sterilizer 12. The light sterilizer 12 includes an upper housing (not shown) and a lower housing 16 interconnected to form a cavity within the housings. The light sterilizer 12 may include a plurality of UVC lights and an LED light positioned within reflectors 42. The reflectors 42 may be mounted to a light printed circuit board assembly (PCBA) 48 that controls the UVC lights, the LED light, or both. The light sterilizer 12 may also include a heat sink 46 abutting each of the UVC lights positioned within the reflectors 42. The heat sinks 46 may help decrease a temperature of the UVC lights during operation by transferring the heat created by the UVC lights through the heat sinks 46, whereby fans 44 connected to the heat sinks 46 may propel the heat away from the device. For example, the air may be pushed out of the one or more slots within the housing of the light sterilizer 12 via the fans 44.

Furthermore, as shown, the heat sinks 46, the fans 44, or both may be directly or indirectly mounted to the light PCBA 48 by one or more fasteners 88.

Furthermore, to ensure proper movement of the light sterilizer 12 and prevent collision, one or more position sensors 36 may be mounted along the light sterilizer 12. The position sensors 36 may be located anywhere along the light sterilizer to detect a position of the light sterilizer 12 relative to one or more obstacles, such as end points of the track 84 or any obstructions along the track 84. As such, the position sensors 36 may be programmed to allow a desired distance between the light sterilizer 12 and any obstacle so that, as the light sterilizer 12 approaches such an obstacle, the position sensors 36 may send a signal to the driver 52 and stop further movement of the light sterilizer 12. It should be noted that the position sensors 36 may be located on opposing sides of the light sterilizer to detect obstacles in any direction of travel.

The light sterilizer 12 may also include a plurality of trolleys 40 secured to the light PCBA 48. The trolleys 40 may engage a track 84 or cable system mounted within a room to allow the light sterilizer 12 to move along the track 84 or cable. For example, as shown in FIG. 7, the trolleys 40 may engage a lip 86 of a track 84 to move the light sterilizer 12 along the track 84. Additionally, to even further ensure proper sterilization of a desired area, one or more of the trolleys 40 may also include an actuator 74. The actuators 74 may be configured to actuate the light sterilizer 12 along a cable (not shown). Thus, the actuators 74 may lower, raise, or both the light sterilizer 12 from the track 84 to advantageously improve the sterilization zone of the light sterilizer 12. It should be note that the actuators 74 may be mounted anywhere along the light sterilizer 12 and/or the track 84 to actuator all or a portion of the light sterilizer 12.

Figure 8:
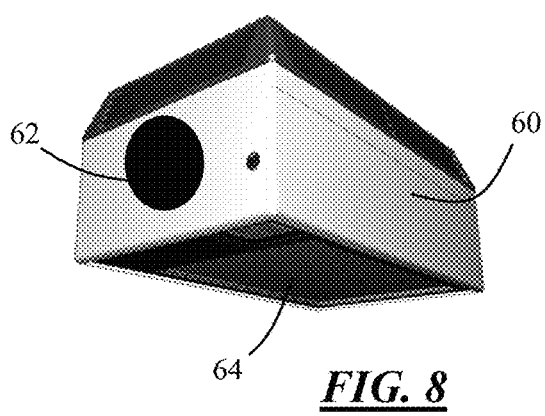
FIG. 8 is a perspective view of an air sterilizer.

FIG. 8 illustrates an air sterilizer 24 as described herein. The air sterilizer 24 may include an intake to direct an air flow into the air sterilizer 24 for sterilizing. After sterilizing, the air may exit a duct 62 and reenter the room. The duct 62 may be any size, shape, and/or orientation. As such, the air sterilizer 24 may beneficially direct the sanitized air anywhere within the room. It should also be noted that the air sterilizer 24 may also be incorporated into the HVAC system of a building and/or room to effectively sterilize the air circulating throughout the room or building. The sterilizing may be completed within the air sterilizer 24 using one or more UVC lights or other sterilizing means. The air sterilizer 24 may be operated congruently with the light sterilizer described herein or may be operated independently. For example, the air sterilizer 24 may continue to operate even when a person is within the room even though the light sterilizer is stopped when a person is present for safety reasons.

Figure 9:
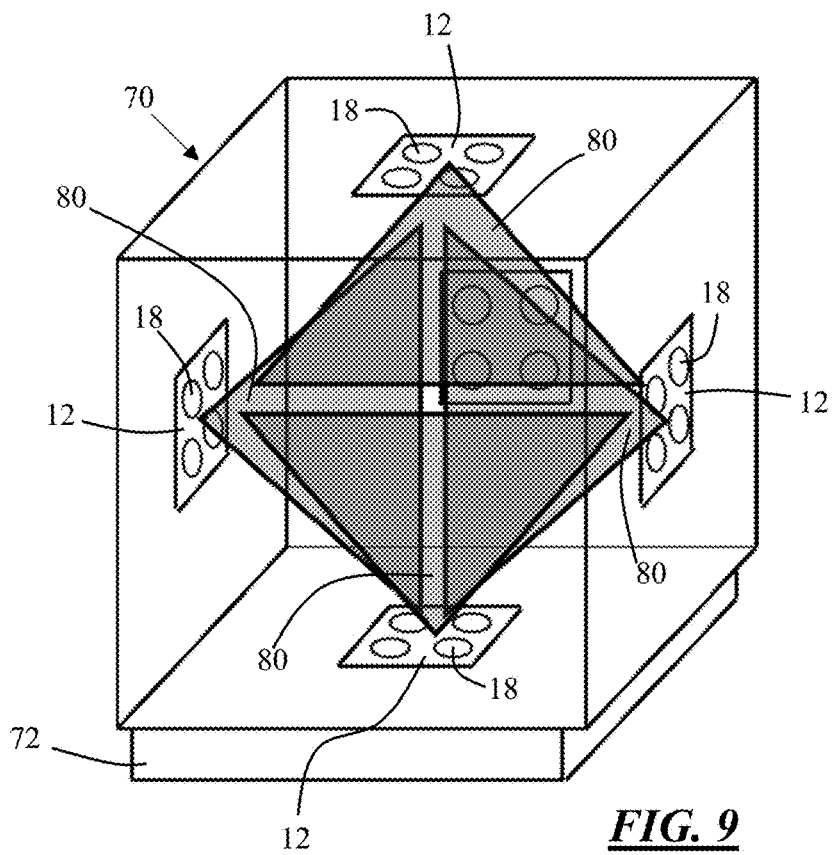
FIG. 9 is a perspective view of a sterilizing chamber.

FIG. 9 illustrates a perspective view of a sterilizing chamber 70 in accordance with the present teachings. The sterilizing chamber 70 may form a chamber substantially enclosed and supported by a base 72. However, the chamber may also be any room, cavity, space, or other area that is targeted for sterilizing. As shown, the sterilizing chamber 70 may include a plurality of light sterilizers 12, each including a plurality of UVC lights 18. It should be noted that the light sterilizers 12 shown have been simplified to more easily portray the sterilizing chamber 70. For example, one or more of the light sterilizers 12 may include an LED light, housing, or other components as described herein (see FIGS. 2-7).

The light sterilizers 12 may be positioned throughout the sterilizing chamber 70 so that a sterilizing zone 80 of each light sterilizer 12 extends into the chamber and at least partially overlaps with other sterilizing zones 80 created by the UVC lights 18. It is envisioned that the light sterilizers 12 may be positioned so that the sterilizing zones 80 created substantially encompass the chamber. For example, at least about 50% or more, about 60% or more, or about 70% or more of the chamber area may be covered by the sterilizing zones 80. Similarly, about 100% or less, about 90% or less, or about 80% or less of the chamber area may be covered by the sterilizing zones 80. Thus, the sterilizing chamber 70 may beneficially sterilize any objects or surfaces within the sterilizing chamber 70.

The light sterilizers 12 may be moveable and/or positionable within the sterilizing chamber 70 to adjust a position of the sterilizing zones 80 created. The light sterilizers 12 may also be integrated into one or more surfaces (e.g., walls) of the sterilizing chamber 70 to simplify assembly, create an optimized area within the chamber, or both.

Additionally, while not shown in FIG. 9, it is envisioned that the sterilizing chamber 70 may include one or more access points, one or more doors, one or more windows, one or more holes, or a combination thereof for entry and removal into the chamber. Furthermore, the sterilizing chamber 70 may be scaled to any desired size based on the sterilizing needs. For example, the sterilizing chamber 70 may be large enough to allow one or more users or one more vehicles to enter the sterilizing chamber 70, or may be sized to allow for easy transportation of the sterilizing chamber 70 between one or more locations.

Figure 10:
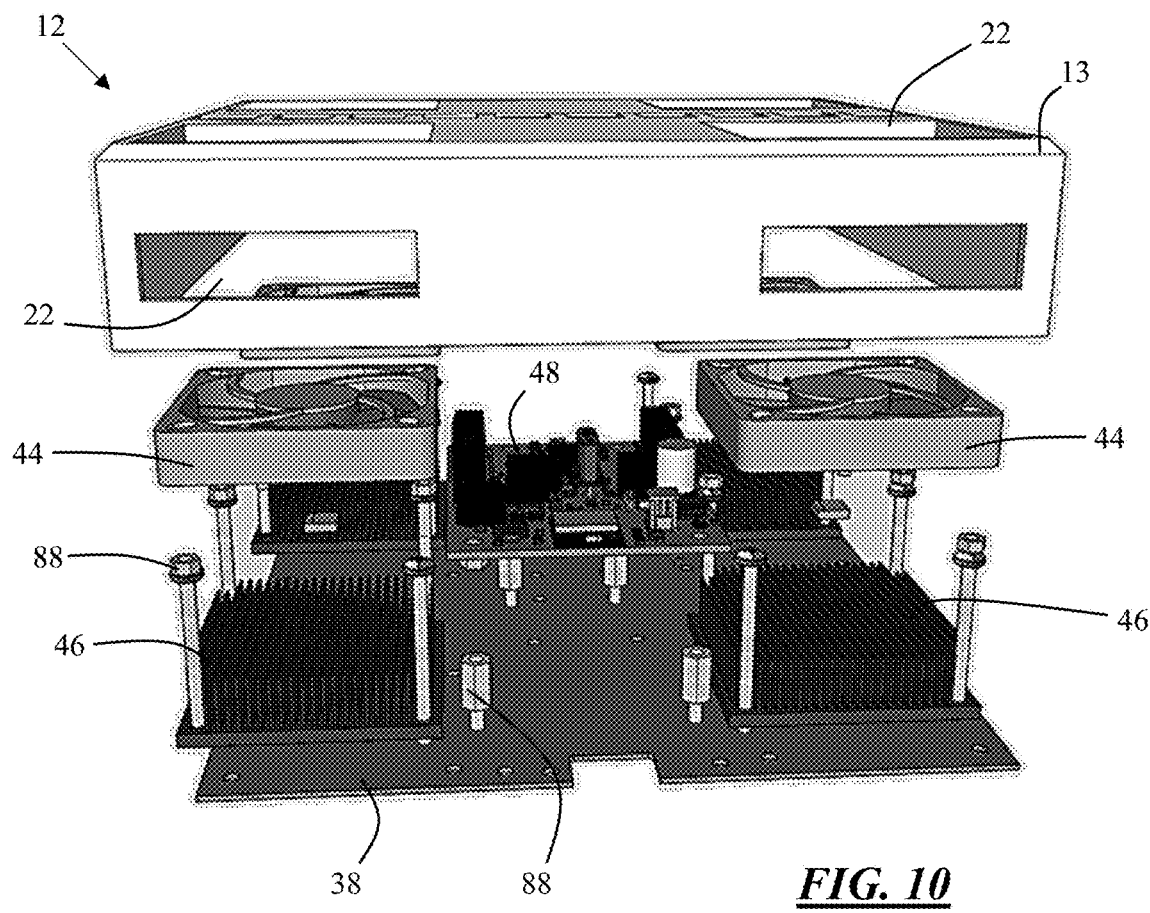
FIG. 10 is an exploded view of a light sterilizer.

FIG. 10 illustrates an exploded view of a light sterilizer 12. It is envisioned that the light sterilizer 12 shown in FIG. 10 may be configured for mounting to a heating, ventilation, and air conditioning (HVAC) system for a vehicle and/or a building. As shown, the light sterilizer 12 may include a plate 38 configured for mounting the light sterilizer to an HVAC or other surface (see FIG. 11). One or more UV-C lights (not shown) may be mounted to the plate 38 and positioned to provide a sanitizing zone within a duct of an HVAC system (see FIG. 11). On an opposing side of the plate 38, a heat sink 46 may be secured via a plurality of fasteners 88 for each UV-C light to provide a thermal management system to maintain an acceptable temperature of the UV-C lights during operation. Similarly, a fan 44 may be adjacent to each heat sink 46 to disperse the heated air created by the UV-C lights and extracted via the heat sink 46. To ensure proper thermal management, a housing 13 may substantially enclose the light sterilizer 12. The housing 13 may also have a plurality of slots 22 to provide ventilation for the heat sinks 46, the fans 44, or both. Additionally, a light printed circuit board assembly (PCBA) may be mounted within the housing 13 to the plate 38 via a plurality of fasteners 88. The light PCBA, as discussed in relation to other figures above, may be configured to control the UV-C lights of the light sterilizer.

Figure 11:
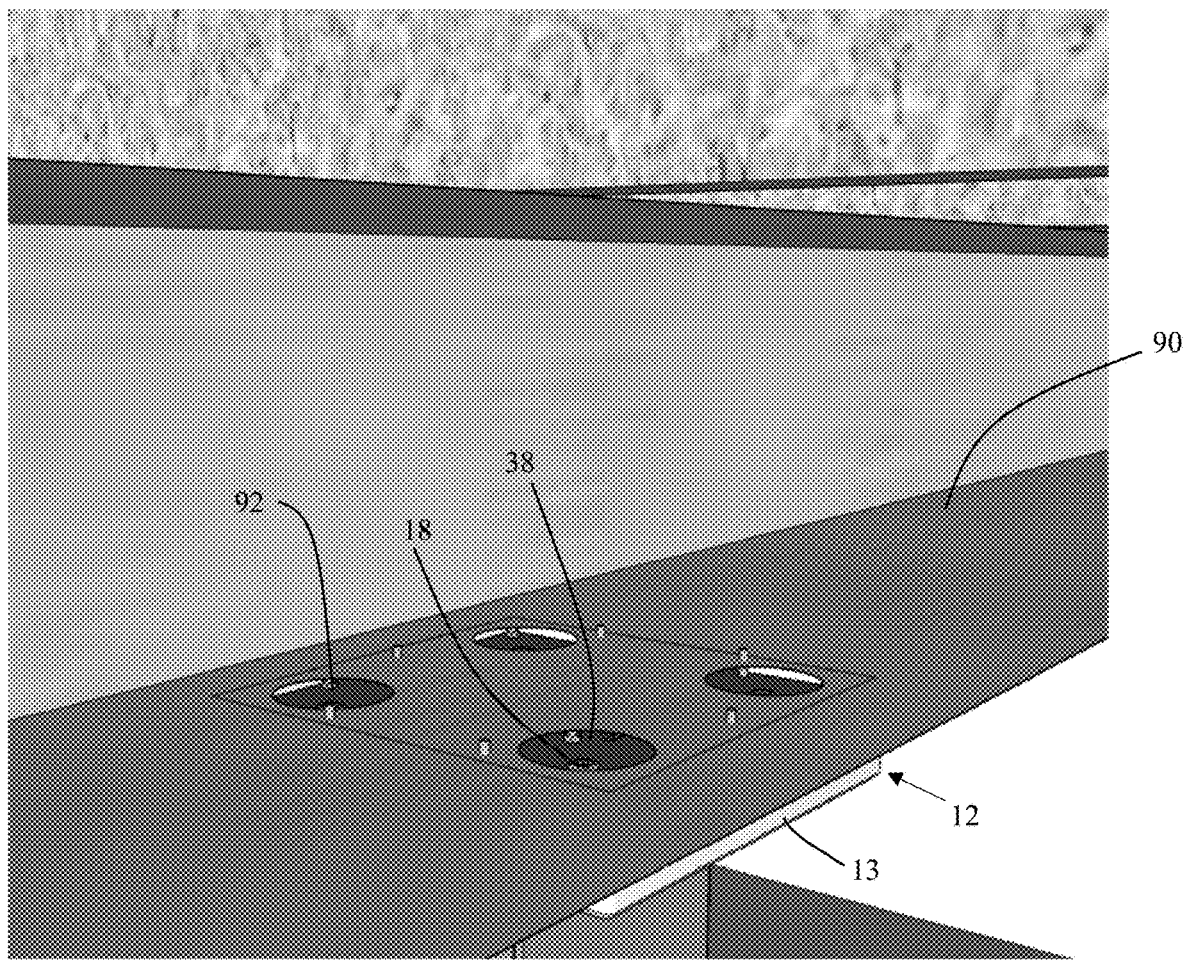
FIG. 11 is a perspective view of the light sterilizer of FIG. 10 mounted to an HVAC duct.

FIG. 11 illustrates a perspective view of the light sterilizer 12 of FIG. 10 mounted to an HVAC duct 90. The housing 13 of the light sterilizer 12 may be positioned outside of the HVAC duct 90 by mounting the plate 38 of the light sterilizer 12 along an outer surface of the HVAC duct 90. As a result, UV-C lights 18 on the abutting surface of the plate 38 may be positioned within cutouts 92 of the HVAC duct 90. Thus, the UV-C lights 18 may create a sterilizing zone within the HVAC duct 90, thereby sterilizing air circulating within the HVAC duct 90.

It should be noted that any configuration of mounting may be implemented for the light sterilizer 12. For example, the light sterilizer 12 may be positioned substantially within the HVAC duct 90 in a path of airflow. Thus, the light sterilizer 12 may have one or more vents or passthrough portions to allow the airflow to continue through the HVAC duct 90 past the light sterilizer.

Figure 12:
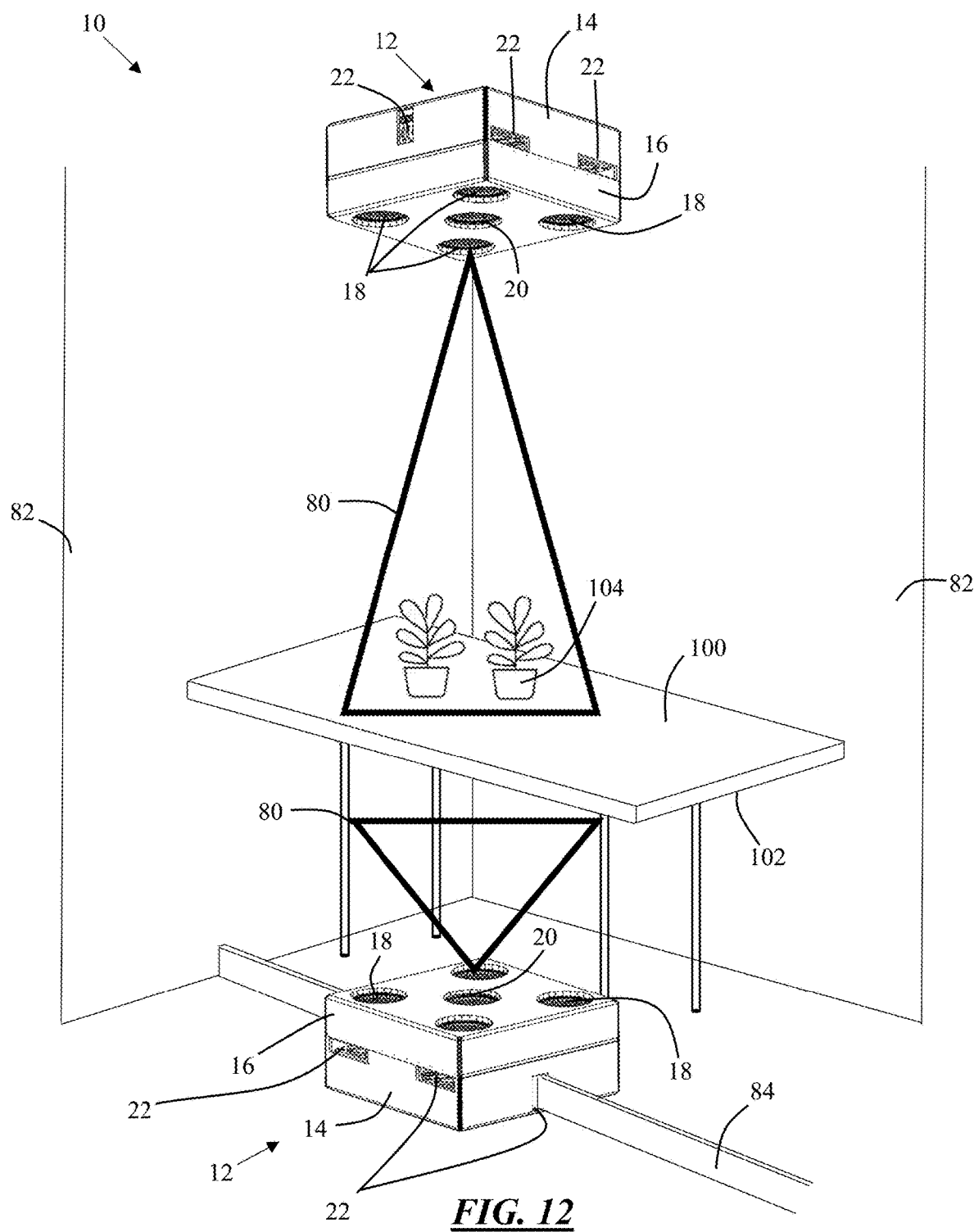
FIG. 12 is a perspective view of a sterilizing system having a plurality of light sterilizers.

FIG. 12 illustrates a perspective view of a sterilizing system 10. The sterilizing system 10 may be configured to sterilizer an area using one or more devices within the sterilizing system 10. An exemplary room at least partially defined by a plurality of walls 82 may be sterilized by the sterilizing system 10.

The sterilizing system may include opposing light sterilizers 12. As shown, the light sterilizers 12 may be mounted along the walls 82 or along a ceiling of the room. Similarly, an opposing light sterilizer 12 may be positioned along a floor of the room. Each light sterilizer 12 may include one or more UVC lights 18 that may cast a sterilizing zone 80 within the room. Beneficially, the opposing light sterilizers 12 may have different sterilizing zones 80 to ensure complete sterilization of one or more objects within the room. For example, a top surface of a table 100 may be sterilized by the light sterilizer 12 positioned on the ceiling while a bottom surface 102 of the table may be sterilized by the light sterilizer 12 positioned on the floor of the room. Advantageously, the dual light sterilizer 12 configuration may sterilize opposing surfaces of objects that may conventionally be difficult to sterilizer.

The light sterilizers 12 may also include an LED light 20 to provide a visual indication of a status of the light sterilizers 12. The UVC lights 18 and the LED light 20 may be at least partially encapsulated in an upper housing 14, a lower housing 16, or both of the light sterilizer 12 that substantially enclose the inner components of the light sterilizer 12. The upper housing 14, the lower housing 16, or both may include one or more slots 22. The slots 22 may function to receive a component that connects to the light sterilizer 12, may provide ventilation to the light sterilizer 12, or both. For example, a track 84 may extend through at least a portion of the slots 22 of the light sterilizer 12 so that the light sterilizer 12 moves along the track (see FIG. 7). It should also be noted that the light sterilizer 12 mounted to the ceiling or upper portion of the walls 82 may also be connected to a track, though not shown in FIG. 12 for simplicity. Similarly, a track 84 may be mounted to one or more walls, a ceiling, a floor, or a combination thereof to ensure that the light sterilizers 12 may move along any desired rooms surfaces. For example, a third light sterilizer 12 may be connected to a track mounted on a wall of the room to even further optimize the sterilizing zones.

While the light sterilizers 12 described herein may provide a means for sterilization, they may also advantageously provide additional functionality. For example, the UVC lights 18 may be tunable to project a desired amount of light onto one or more plants 104 positioned within the sterilizing zone 80. As such, the light sterilizers 12 may beneficially promote optimized growth of plants 104 (i.e., cannabis, agricultural plants such as produce or grains, etc.) while also being able to sterilize the growing area, thereby preventing pathogens or harmful particulars from compromising the health of the plants 104. Thus, it may be gleaned from the present teachings that the light sterilizers 12 may beneficially provide sterilization and optimized growing conditions for various aspects of an industry—farming and/or growing, processing, distribution and logistics, retail, or a combination thereof. For example, the light sterilizers 12 may be utilized to ensure a sterilized environment by killing and/or preventing contaminants, such as bacteria, insect infiltration, mold growth, foodborne disease (e.g., salmonella), or a combination thereof during manufacturing and/or harvesting (e.g., farming), during food storage at a warehouse or retail environment, or a combination thereof.

Figure 13:
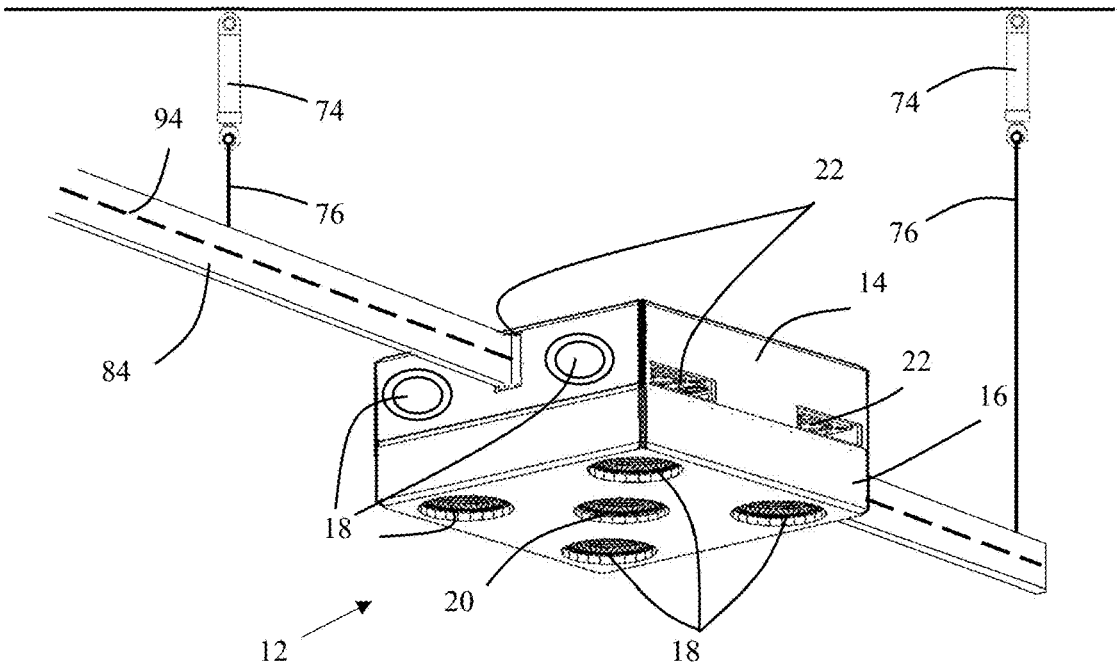
FIG. 13 is a perspective view of a light sterilizer having a secondary circuit.

FIG. 13 illustrates a perspective view of a light sterilizer 12. As described above, the light sterilizer 12 may include a plurality of UVC lights 18 and one or more LED lights 20. The UVC lights 18 and the LED light 20 may be at least partially encapsulated in an upper housing 14, a lower housing 16, or both of the light sterilizer 12 that substantially enclose the inner components of the light sterilizer 12. For example, the UVC lights 18 may be located along a bottom portion of the lower housing 16, one or more sides of the upper housing 14, a top portion of the upper housing 14 (not shown), or a combination thereof. Thus, the UVC lights 18 may be positioned anywhere along the light sterilizer 12 to ensure proper sterilization coverage of a desired area. The upper housing 14, the lower housing 16, or both may also include one or more slots 22. The slots 22 may function to receive a component, such as a track 84 that connects to the light sterilizer 12, may provide ventilation to the light sterilizer 12, or both.

While the light sterilizer 12 may move along the track 84, the track 84 itself may also actuate due to communication with one or more actuators 74 connected to a wall or ceiling. As illustrated, the actuators 74 may be secured to a ceiling to raise and/or lower the entire track 84 and light sterilizer 12 relative to the ceiling along cables 76. Beneficially, the light sterilizer 12 may still move along the track 84 independent of the positioning of the track 84 due to actuator by the one or more actuators 74.

The light sterilizer 12 may be in communication with a secondary circuit 94 to power one or more secondary lights. For example, it is envisioned that the light sterilizer 12 may also include one or more white lights contained within the upper housing 14 and/or the lower housing 16. While the UVC lights 18 and the LED light 20 may be powered by a primary circuit, the white lights may be independently powered by the secondary circuit 94 to allow for the white lights to be operated when the remainder of the light sterilizer 12 is turned off. Beneficially, the light sterilizer 12 may be operated on the primary circuit for sterilizing purposes but may be fully shut off for safety reasons (i.e., to ensure no UVC light is present when one or more individuals are present in the sterilizing zone). While the UVC lights are shut off, the white lights may be powered by the secondary circuit 94, thereby providing a work light or decor light for the room. Beneficially, the light sterilizer 12 may provide a single device to operate as both a sterilizing device and as a conventional room light. Thus, a user may no longer be required to purchase or position an additional light source within the room.

The white lights (not shown) may be mounted to the light printed circuit board assembly (PCBA) similar to the additional LED lights 20 providing a status indication for the light sterilizer 12 (see FIGS. 4-6). As such, the white lights may be additional LED lights connected to the secondary circuit 94. However, the white lights may also be any other type of light, such as a halogen light, a compact fluorescent light (CFL), fluorescent light, or a combination thereof. Thus, the light sterilizer 12 may beneficially providing a packaging means for any white lights required for a given application or desired room.

Figure 14:
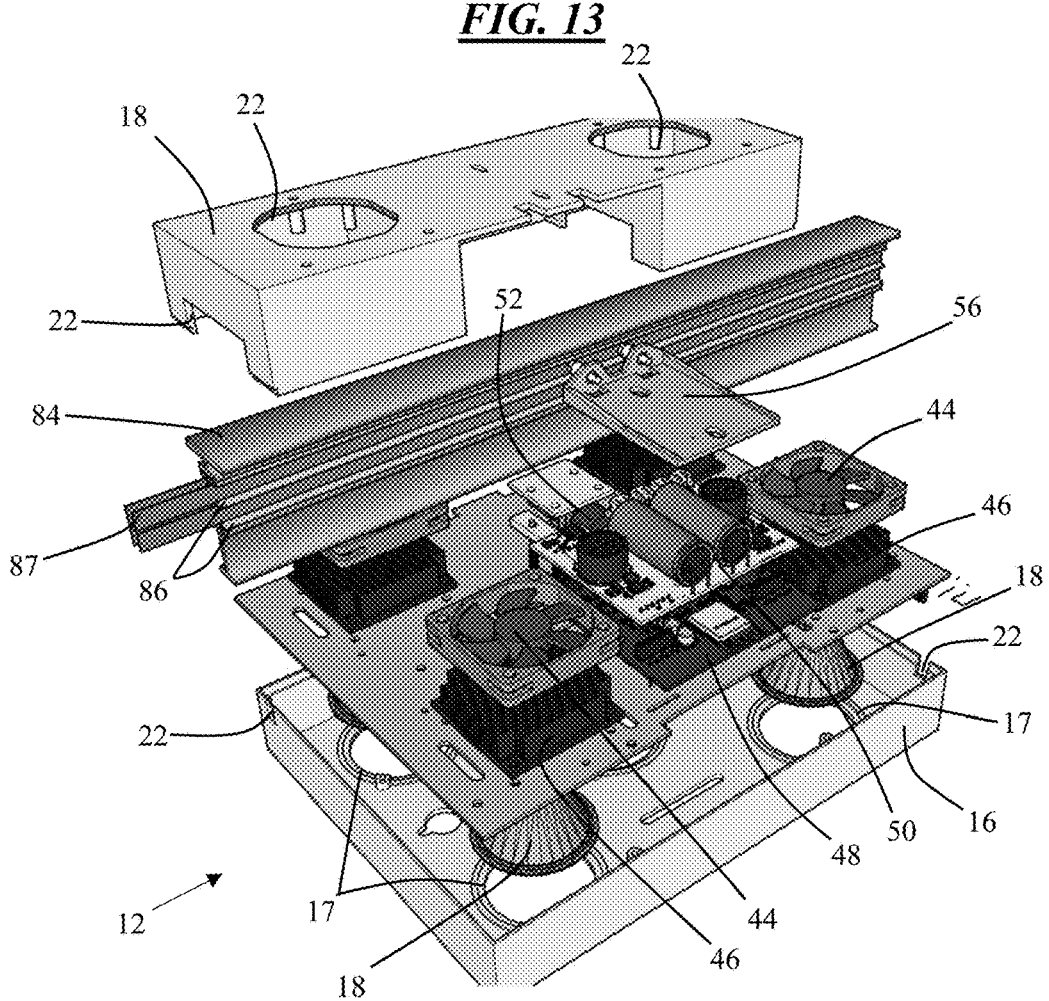
FIG. 14 is an exploded view of a light sterilizer.

FIG. 14 illustrates an exploded view of a light sterilizer 12 in accordance with the present teachings. The light sterilizer 12 includes an upper housing 18 and a lower housing 16 interconnected to form a cavity therein. The light sterilizer 12 may include a plurality of UVC lights and/or an LED light positioned within reflectors 42. The reflectors 42 may be mounted to a light printed circuit board assembly (PCBA) 48 such that the reflectors 42 align with apertures 17 (e.g., holes and/or cutouts) along the lower housing 16. The light sterilizer 12 may also include a heat sink 46 abutting each of the UVC lights (not shown) positioned within the reflectors 42. The heat sinks 46 may alleviate heightened temperatures caused by the UVC lights during operation by transferring the heat through the heat sinks 46, whereby fans 44 adjacent to the heat sinks 46 expel the excess heat away from the device through one or more slots 22 in the upper housing 18.

As discussed above, the light sterilizer 12 may be guided along a track 84 or other type of guidance system. As shown, a track 84 may extend through an upper housing 18 and/or a lower housing 16 via one or more slots 22 so that trolleys or bearings (not shown; see, e.g., FIG. 7) of the light sterilizer 12 engage one or more lips 86 along the track 84. Similarly, the light sterilizer 12 may also include a biasing member 56 having a bracket or other connection means to secure the biasing member 56 to the light sterilizer 12. The biasing member 56 may be in communication with the one or more lips 86 or a spacer 87 positioned between the lips 86 to ensure proper engagement between the trolley of the light sterilizer 12 and the track 84. Thus, the biasing member 56 may help a driver 52 controlled by a trolley driver printed circuit board assembly (PCBA) 50 to properly guide the light sterilizer 12 along the track 84.

Figure 15A:
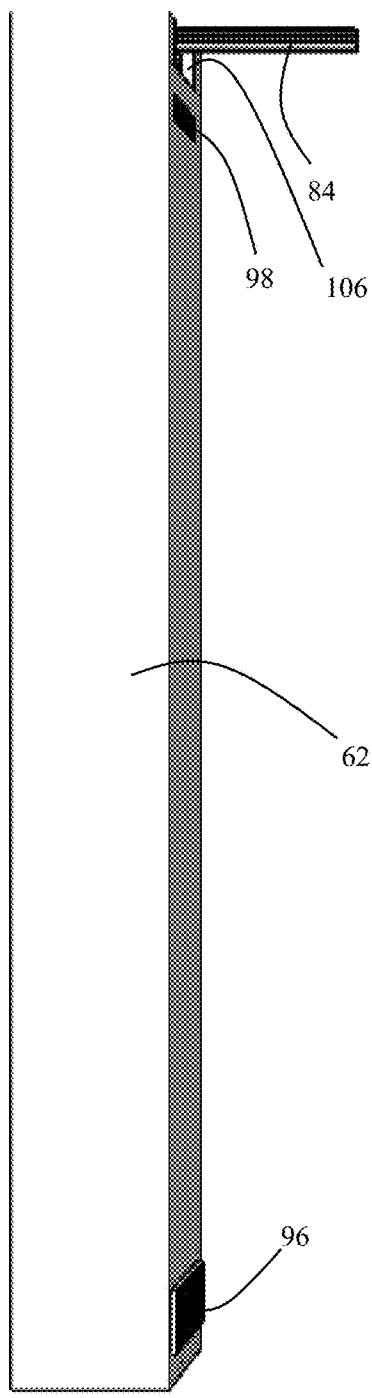
FIG. 15A is a perspective view of a light sterilizer positioned within an HVAC duct.
Figure 15B:
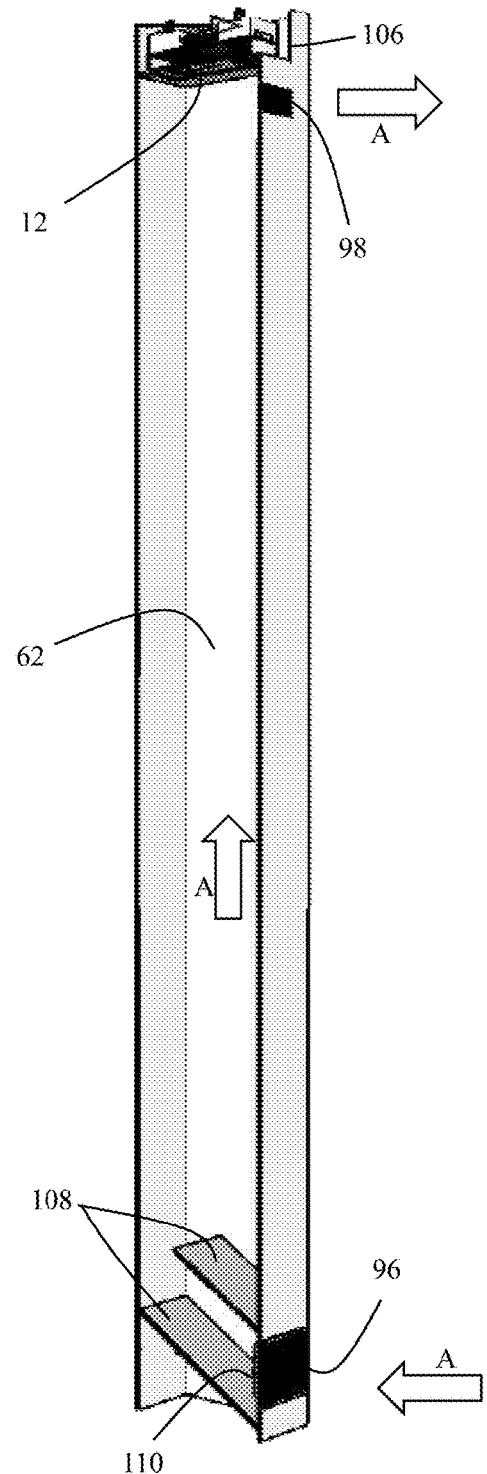
FIG. 15B is a sectional perspective view of the light sterilizer within the HVAC duct as shown in FIG. 15A.

FIGS. 15A and 15B illustrates a perspective view and a cross-sectional view, respectively, of a light sterilizer 12 within a duct 62 in accordance with the present teachings. As discussed above, the light sterilizer 12 may be adapted for sterilizing a room separate from an HVAC system (e.g., FIG. 1) or may be integrated into an existing HVAC system (e.g., FIG. 11). Similarly, the light sterilizer 12 may also be at least partially in communication with a duct 62 of an HVAC system—or an independent duct 62 separate from the HVAC system). As a result, the light sterilizer 12 may advantageously maintain movement along a track 84 to sterilize a room when a person is not present to ensure safety yet provide sterilization of the room. However, when a person is present in the room, the light sterilizer 12 may beneficially maintain sterilization of the room by moving along the track 84 into an opening 106 of the duct 62. As a result, the light sterilizer 12 may still be turned on to sterilize the air in a room, yet due to the positioning within the duct 62, a person located within the room may not be exposed to the light from the light sterilizer 12.

As shown, the duct 62 may include a return vent 96 and a supply vent 98. The return vent 96 may be positioned near a base of the duct 62 to capture a downdraft of air within the room. The return vent 96 may also include an intake impeller 110 that promotes the intake of air into the duct 62. The intake impeller 110 may be a fan or other device that is adapted to help suck in air from the surrounding room into the return vent 96. Once the air is within the duct 62, the air moves upwards in direction (A) towards the light sterilizer 12 so that the light sterilizer 12 may effectively sterilize the air prior to reaching the supply vent 98. Similarly, to further ensure effective sterilization, one or more reflective surfaces 108, such as mirrors, reflective metal surfaces, etc., may be positioned near the base of the duct 62. As a result, light emitted from the light sterilizer 12 may not only directly contact particles within the air but may also bounce off the reflective surfaces 108 to return towards the light sterilizer 12 and further contact said particles (e.g., pathogens, viruses, etc.). It should be noted that the reflective surfaces 108 may be positioned at any desired angle or location within the duct 62. Once the air has been sterilized, the air is moved out of the supply vent 98 back into the room.

Additionally, it should be noted that the light sterilizer 12 may be positioned within the duct 62 or outside of the duct 62 based on any desired programming, timing, schedule, or a combination thereof. That is, the light sterilizer 12 may be configured to meet the demands of a given building to properly sterilize the room in the most effective manner. Similarly, while the return duct 96 is positioned near a base of the duct 62, the return duct 96 may also be positioned near the light sterilizer 12 so that the air intake happens near the top of the duct 62 and is forced through the duct 62 towards a base where a supply vent 98 may be located. Moreover, if the duct 62 is integrated into a building HVAC system, an intake impeller 110 may not be necessary, as a fan from the HVAC system may be sufficient to take in the air through the return duct 96. Thus, configurations may vary based on different applications.

It should be noted that the sterilizing system described herein may include any number of devices as detailed above. For example, a sterilizing system may include a plurality of light sterilizers or a single light sterilizer. Similarly, the sterilizing system may include a plurality of air sterilizers or a single air sterilizer. Similarly, any device within the sterilizing system may be used separated and independently of any other devices of the sterilizing system. For example, the light sterilizer may be used independent so that the light sterilizer may be integrated into a chamber, room, or ducting for more specific sterilizing needs. As such, it may be gleaned from the present teachings that sterilizing system is beneficially highly customizable and tunable to meet the needs of an end-user.

ELEMENT LIST

10 Sterilizing System
12 Light Sterilizer
13 Housing
14 Upper Housing
16 Lower Housing
17 Housing Aperture
18 UVC Light
20 LED Light
22 Slot
24 Air Sterilizer
26 Mobile Device
28 Emergency Stop
30 Room Sensor
32 Radar Sensor
34 Infrared (IR) Sensor
36 Position Sensor
38 Plate
40 Trolley
42 Reflector
44 Fan
46 Heat Sink
48 Light Printed Circuit Board Assembly (PCBA)
50 Trolley Driver Printed Circuit Board Assembly (PCBA)
52 Driver
54 Drive Motor
56 Biasing Member
60 Air Sterilizer Housing
62 Duct
64 Intake
70 Sterilizing Chamber
72 Base 74 Actuator
76 Cable
80 Sterilizing Zone
82 Wall
84 Track
86 Lip
87 Spacer
88 Fastener
90 HVAC Duct
92 Cutout
94 Secondary Circuit
96 Return Vent
98 Supply Vent
100 Table Top Surface
102 Table Bottom Surface
104 Plant
106 Opening
108 Reflective Surface
110 Intake Impeller
I Direction of Air Intake of the Air Sterilizer
R Direction of Air Return from the Air Sterilizer
A Direction of Airflow in Duct Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time, and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements, ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Unless otherwise stated, a teaching with the term "about" or "approximately" in combination with a numerical amount encompasses a teaching of the recited amount, as well as approximations of that recited amount. By way of example, a teaching of "about 100" encompasses a teaching of 100 +/−15.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. A light sterilizer comprising:
   (a) an ultraviolet-C (UVC) light secured to a light printed circuit board assembly (PCBA), wherein the UVC light projects a sterilizing zone to sterilize objects or surfaces within the sterilizing zone;
   (b) a heat sink positioned adjacent to and in contact with the UVC light, wherein the heat sink is mounted to the light PCBA; and
   (c) a fan positioned adjacent to the heat sink;
   (d) a trolley that is configured to guide the light sterilizer along a track or cable system;
   wherein the trolley is located within a housing of the light sterilizer and the track or cable system extends through a slot of the housing to engage the trolley; and
   wherein the UVC light sterilizes viruses within the sterilizing zone by breaking the virus molecules.

2. The light sterilizer of claim 1, further comprising a reflector, wherein the UVC light is positioned within the reflector.

3. The light sterilizer of claim 2, wherein, the light PCBA is positioned within a housing that at least partially encompasses the light PCBA and the UVC light.

4. The light sterilizer of claim 1, wherein the light sterilizer includes an LED light secured to the light PCBA, and the LED light indicates a status of the light PCBA.

5. The light sterilizer of claim 4, wherein the LED light is positioned within a reflector.

6. The light sterilizer of claim 5, wherein the reflector is secured to a housing of the light sterilizer.

7. The light sterilizer of claim 1, wherein the light sterilizer includes a driver located within the housing of the light sterilizer that engages the track or the cable system, and the driver is actuated by a drive motor to move the light sterilizer along the track or the cable system.

8. The light sterilizer of claim 1, wherein the heat sink and the fan are contained within the housing of the light sterilizer, and the heat sink is vented to an outside of the housing via a slot in the housing.

9. The light sterilizer of claim 8, including a reflector that is tiltable, flexible, or both.

10. The light sterilizer of claim 1, wherein the light sterilizer includes four or more UVC lights, and each of the UVC lights creates their own sterilizing zone.

11. The light sterilizer of claim 10, wherein each sterilizing zone at least partially overlaps with another sterilizing zone.

12. The light sterilizer of claim 11, wherein the light sterilizer includes one or more position sensors to determine a position of the light sterilizer during movement along the track or the cable system.

13. A sterilizing system comprising:
   (a) a light sterilizer according to claim 1;
   (b) an air sterilizer that circulates and sterilizes air within a desired area or room;
   (c) one or more room sensors, wherein the one or more room sensors detect the presence of a person within the desired area or room and communicates the detection with the light sterilizer.

14. The sterilizing system of claim 13, wherein the air sterilizer includes:
   (a) an intake that receives the air from the desired area or room;
   (b) a sterilizing device within a housing of the air sterilizer that sterilizes the air received from the intake; and
   (c) a duct that distributes the sterilized air back into the desired area or room.

15. The sterilizing system of claim 14, wherein the sterilizing device is a UVC light.

16. The light sterilizer of claim 1, including an ultraviolet-B (UVB) light.

17. The light sterilizer of claim 1, including lights having wavelengths of from 100 nm to 400 nm.

18. The light sterilizer of claim 1, including a mobile device having software or an application adapted to control one or more of schedule of the light sterilizer, intensity of the light sterilizer, cycling on and/or off the sterilizer, emergency shutoff of the light sterilizer, diagnostics mode of the light sterilizer, and movement of the light sterilizer.

19. The light sterilizer of claim 1, including one or more wheels.

* * * * *